US010143766B2

(12) United States Patent
Gruenbacher et al.

(10) Patent No.: US 10,143,766 B2
(45) Date of Patent: Dec. 4, 2018

(54) VOLATILE COMPOSITION DISPENSER

(75) Inventors: Dana Paul Gruenbacher, Fairfield, OH (US); Bryan Gabriel Comstock, Mason, OH (US); James Douglas Still, Cleves, OH (US); Rainer Bernhard Teufel, Worthington, OH (US); Richard Lee Lane, Columbus, OH (US); Walter Sordo, Trenton (IT); Danilo Rossi, Trenton (IT)

(73) Assignee: The Procter & Gamble Company, Cincinnati, OH (US)

( * ) Notice: Subject to any disclaimer, the term of this patent is extended or adjusted under 35 U.S.C. 154(b) by 581 days.

(21) Appl. No.: 12/760,848

(22) Filed: Apr. 15, 2010

(65) Prior Publication Data

US 2010/0314461 A1 Dec. 16, 2010

Related U.S. Application Data

(60) Provisional application No. 61/169,840, filed on Apr. 16, 2009.

(51) Int. Cl.
*A61L 9/12* (2006.01)
*A01N 25/18* (2006.01)
*B60H 3/00* (2006.01)

(52) U.S. Cl.
CPC .............. *A61L 9/12* (2013.01); *B60H 3/0028* (2013.01); *A61L 2209/131* (2013.01); *B60H 2003/0057* (2013.01)

(58) Field of Classification Search
CPC . A61L 9/12; A61L 9/042; A61L 9/127; A61L 2209/131; A01N 25/18;
(Continued)

(56) References Cited

U.S. PATENT DOCUMENTS 3,169,665 A * 2/1965 Colley .............................. 222/5
3,351,495 A 11/1967 Larsen et al.
(Continued)

FOREIGN PATENT DOCUMENTS

EP 1118338 A2 7/2001
FR 1231135 9/1960
(Continued)

OTHER PUBLICATIONS

Refresh your day—Air Freshners for your home, car, and office. http://www.refreshyourday.com/products/php HandStands, 675 W 14800, S Bluffdale, UT 84065; Apr. 16, 2009.
(Continued)

*Primary Examiner* — Chee-Chong Lee
(74) *Attorney, Agent, or Firm* — Abbey A. Lopez

(57) ABSTRACT

A volatile composition dispenser comprises a volatile composition container comprising at least one volatile composition therein. A rupture element is positioned proximate to the volatile composition container. The volatile composition container comprises a cam comprising a camming surface. The camming surface is configured to move at least a portion of the rupture element toward the volatile composition container to puncture the volatile composition container and release at least a portion of the volatile composition from the volatile composition container such that the portion of the volatile composition evaporates and exits the volatile composition dispenser.

8 Claims, 19 Drawing Sheets

(58) Field of Classification Search
CPC .............. A01M 1/2044; A01M 1/2055; A01M 31/008; B60H 3/0007; B65D 85/00
USPC ........ 239/6, 51, 41, 42, 43; 222/81–85, 223, 222/228, 247
See application file for complete search history.

(56) References Cited

U.S. PATENT DOCUMENTS

| | | | |
|---|---|---|---|
| 3,727,840 A * | 4/1973 | Nigro | 239/43 |
| 4,161,283 A | 7/1979 | Hyman | |
| 4,161,284 A * | 7/1979 | Rattan | 239/43 |
| 4,339,079 A | 7/1982 | Sato et al. | |
| 4,387,849 A * | 6/1983 | Van Loveren et al. | 239/6 |
| 4,526,320 A | 7/1985 | Von Philipp et al. | |
| 4,630,775 A * | 12/1986 | Mandon et al. | 239/56 |
| 4,762,275 A | 8/1988 | Herbert | |
| 4,824,707 A | 4/1989 | Spector | |
| 4,947,578 A | 8/1990 | Anderson | |
| 4,995,555 A * | 2/1991 | Woodruff | 239/43 |
| 5,000,383 A * | 3/1991 | van der Heijden | 239/47 |
| 5,230,867 A | 7/1993 | Kunze et al. | |
| 5,253,008 A | 10/1993 | Konishi et al. | |
| 5,455,043 A | 10/1995 | Fischel-Ghodsian | |
| 5,749,520 A | 5/1998 | Martin | |
| 5,875,968 A | 3/1999 | Miller | |
| 6,553,712 B1 | 4/2003 | Majerowski | |
| 6,583,106 B2 | 6/2003 | Zofchak | |
| 7,481,380 B2 | 1/2009 | Kvietok et al. | |
| 7,498,369 B2 | 3/2009 | Whear et al. | |
| 7,754,938 B2 | 7/2010 | Rashid | |
| 7,883,028 B2 | 2/2011 | McGee et al. | |
| 8,696,982 B2 | 4/2014 | Gruenbacher et al. | |
| 8,709,337 B2 | 4/2014 | Gruenbacher et al. | |
| 8,740,110 B2 | 6/2014 | Gruenbacher | |
| 8,931,711 B2 | 1/2015 | Gruenbacher et al. | |
| 9,272,063 B2 | 3/2016 | Gruenbacher et al. | |
| 2003/0089791 A1 | 5/2003 | Chen | |
| 2003/0190255 A1 | 10/2003 | Boden | |
| 2004/0003724 A1 | 1/2004 | Ellis | |
| 2005/0095264 A1 | 5/2005 | Tollens et al. | |
| 2005/0127538 A1 | 6/2005 | Fabrega et al. | |
| 2005/0211790 A1 | 9/2005 | Kvietok et al. | |
| 2005/0247802 A1 | 11/2005 | Varanasi | |
| 2006/0076429 A1 | 4/2006 | Kvietok et al. | |
| 2006/0097065 A1 | 5/2006 | Kvietok et al. | |
| 2006/0097066 A1 | 5/2006 | Kvietok et al. | |
| 2006/0121269 A1 | 6/2006 | Miller et al. | |
| 2006/0175425 A1 | 8/2006 | McGee et al. | |
| 2006/0231641 A1 | 10/2006 | Uchiyama et al. | |
| 2006/0233538 A1 | 10/2006 | Tollens et al. | |
| 2006/0237555 A1 | 10/2006 | Cetti et al. | |
| 2007/0237498 A1* | 10/2007 | Helf et al. | 392/386 |
| 2008/0191050 A1 | 8/2008 | Blondeau et al. | |
| 2009/0188986 A1 | 7/2009 | Blondeau et al. | |
| 2010/0154822 A1* | 6/2010 | Reed et al. | 134/6 |
| 2010/0264232 A1 | 10/2010 | Gruenbacher et al. | |
| 2010/0308130 A1 | 12/2010 | Gruenbacher | |
| 2011/0180621 A1 | 7/2011 | Gruenbacher | |
| 2014/0197246 A1 | 3/2014 | Gruenbacher et al. | |

FOREIGN PATENT DOCUMENTS

| | | |
|---|---|---|
| JP | 61051833 | 3/1986 |
| JP | 61051834 | 3/1986 |
| JP | 63184040 | 7/1988 |
| JP | 03070139 | 3/1991 |
| JP | 05029540 | 2/1993 |
| JP | A-H5-345832 | 12/1993 |
| JP | 07037188 | 2/1995 |
| JP | 10085313 | 4/1998 |
| JP | 2005-029540 | 2/2005 |
| JP | 2005-261805 | 9/2005 |
| JP | A-2005-239772 | 9/2005 |
| JP | 2006-247479 | 9/2006 |
| JP | A-2008-056613 | 3/2008 |
| JP | 2008-087816 | 4/2008 |
| WO | WO 88/08721 | 11/1988 |
| WO | WO 9712518 A1 | 4/1997 |
| WO | WO 98/16262 | 4/1998 |
| WO | WO 98/16262 A1 | 4/1998 |
| WO | WO 2006/007559 A2 | 1/2006 |
| WO | WO 2006/029252 A1 | 3/2006 |
| WO | WO 2008/038706 | 3/2008 |
| WO | WO 2009/024802 A1 | 2/2009 |
| WO | WO 2009/024802 A1 | 6/2009 |

OTHER PUBLICATIONS

Autoexpressions air care vent-it vent stix, http://www.autoexpressions.com/air-care/vent-it/vent-stix/cherry SOPUS Products, 609 Science Drive, Moorpark, CA 93065; Apr. 16, 2009.
ScentPortable Clip & Go Fragrance Unit, Slatkin & Co., 610 Broadway Ste 4, New York, NY 10012; Apr. 23, 2009.
Off! Clip-On Mosquito Repellent, http://offprotects.com/clip-on-mosquito-repellent/ SC Johnson, 1525 Howe Street, Racine, Wisconsin 53403-5011; Jun. 29, 2009.
U.S. Appl. No. 29/335,463, filed Apr. 16, 2009, Koenig, et al.
U.S. Appl. No. 29/341,622, filed Aug. 10, 2009, Koenig, et al.
U.S. Appl. No. 29/351,724, filed Dec. 10, 2009, Koenig, et al.
U.S. Appl. No. 12/694,637, filed Jan. 27, 2010, Gruenbacher, et al.
U.S. Appl. No. 12/760,578, filed Apr. 15, 2010, Gruenbacher, et al.
U.S. Appl. No. 12/724,442, filed Mar. 16, 2010, Gruenbacher, et al.
U.S. Appl. No. 12/760,580, filed Apr. 15, 2010, Gruenbacher, et al.
All Office Actions, U.S. Appl. No. 14/217,955.
All Office Actions, U.S. Appl. No. 15/005,224.

* cited by examiner

VOLATILE COMPOSITION DISPENSER

CROSS REFERENCE TO RELATED APPLICATIONS

The present application claims the benefit of U.S. Provisional Application No. 61/169,840, filed on Apr. 16, 2009.

FIELD

The present disclosure relates to methods and apparatuses for dispensing a volatile composition and, more particularly, relates to methods and apparatuses for dispensing a volatile composition using a membrane.

BACKGROUND

A volatile composition dispenser can be used to evaporate a volatile composition into an atmosphere, such as a domestic atmosphere or a vehicle passenger compartment atmosphere, for example, in order to deliver a variety of benefits, such as air freshening or perfuming of the atmosphere. Non-energized dispensing systems, for example, systems that are not powered by electrical energy, are a popular way for delivery of the volatile composition into the atmosphere. These dispensing systems can be classified into those that may require human actuation, such as aerosols, and those that may not require human actuation, such as wick-based systems and gels. The first type of dispensing system delivers the volatile composition on demand, while the second type of dispensing system delivers the volatile composition in a more continuous manner. Because of the wide spread demand for and use of volatile composition dispensers, the volatile composition dispenser technology should be improved.

SUMMARY

In one non-limiting embodiment, a volatile composition dispenser comprises a volatile composition container comprising at least one volatile composition therein. A rupture element is positioned proximate to the volatile composition container. The volatile composition dispenser comprises a cam comprising a camming surface. The camming surface is configured to move at least a portion of the rupture element toward the volatile composition container to puncture the volatile composition container and release at least a portion of the volatile composition from the volatile composition container such that the portion of the volatile composition evaporates and exits the volatile composition dispenser.

In another non-limiting embodiment, a volatile composition dispenser comprises an outer shell and a volatile composition container comprising at least one volatile composition therein. The volatile composition container is configured to be at least partially positioned within the outer shell. The volatile composition dispenser further comprises an element comprising a puncturing member positioned proximate to the volatile composition container and an actuator configured to move at least the puncturing member toward the volatile composition container to puncture the volatile composition container and release at least a portion of the volatile composition from the volatile composition container such that the portion of the volatile composition evaporates and exits the outer shell.

In yet another non-limiting embodiment, a volatile composition dispensing system comprises a volatile composition container comprising at least one volatile composition therein and a rupture element comprising a movable portion. The rupture element is positioned proximate to the volatile composition container. The volatile composition dispensing system further comprises a breathable membrane positioned proximate to the rupture element and an actuator configured to move between a first position, where the actuator is free from applying a force to the movable portion, and a second position, where the actuator applies a force to the movable portion to cause the movable portion to be forced towards the volatile composition container to puncture the volatile composition container and release at least a portion of the volatile composition onto the breathable membrane for evaporation.

In still another non-limiting embodiment, a volatile composition cartridge for a volatile composition dispenser comprises a volatile composition container comprising at least one volatile composition therein, a rupture element positioned proximate to the volatile composition container, and a microporous membrane positioned proximate to the rupture element. The rupture element is sealably engaged with a portion of the volatile composition container and a portion of the microporous membrane. The rupture element, upon activation, is configured to create an aperture in the volatile composition container to release the volatile composition from the volatile composition container onto the microporous membrane.

In still another non-limiting embodiment, a method of dispensing a volatile composition comprises providing a volatile composition container comprising a volatile composition therein and providing a rupture element positioned proximate to the volatile composition container. The method further comprises actuating an actuator to move at least a portion of the rupture element and puncture the volatile composition container such that at least a portion of the volatile composition is released from the volatile composition container for evaporation.

BRIEF DESCRIPTION OF DRAWINGS

The above-mentioned and other features and advantages of the present disclosure, and the manner of attaining them, will become more apparent and the disclosure itself will be better understood by reference to the following description of embodiments taken in conjunction with the accompanying drawings, wherein.

DETAILED DESCRIPTION

Figure 1:
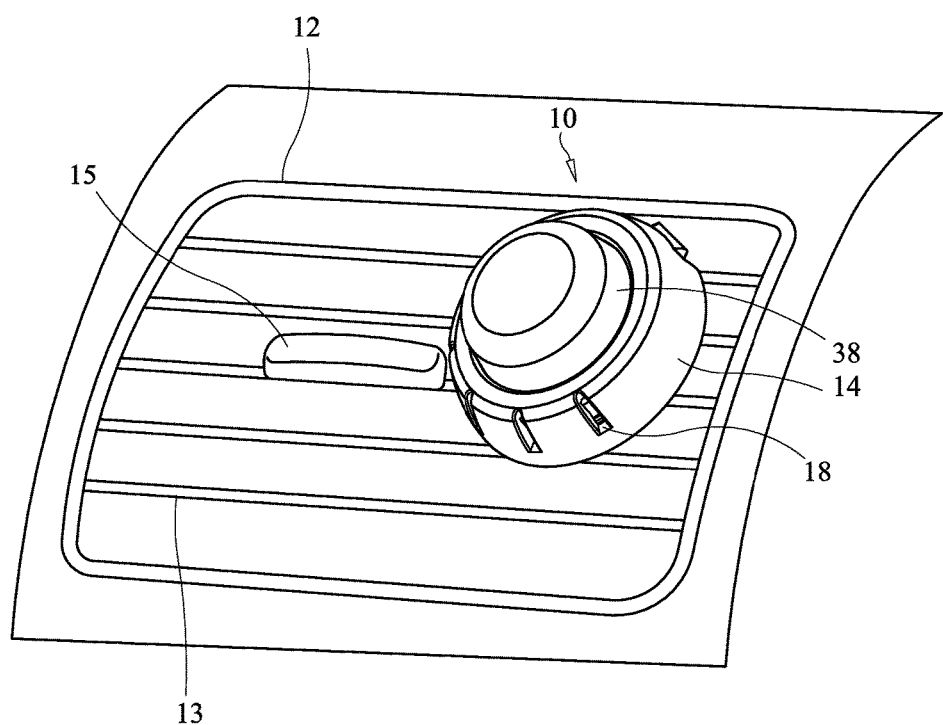
FIG. 1 is a perspective view of a volatile composition dispenser positioned on an air system vent of a vehicle in accordance with one non-limiting embodiment.
Figure 2:
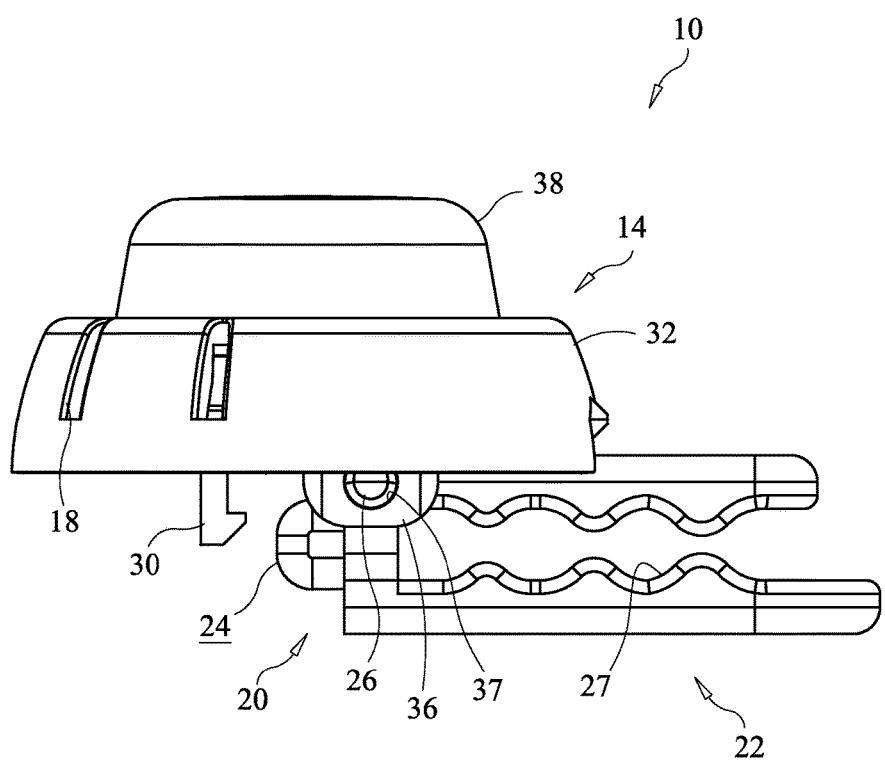
FIG. 2 is a side view of a volatile composition dispenser, with a cam in a first, non-actuated position in accordance with one non-limiting embodiment.

Various embodiments will now be described to provide an overall understanding of the principles of the structure, function, manufacture, and use of the apparatuses and methods disclosed herein. One or more examples of these embodiments are illustrated in the accompanying drawings. Those of ordinary skill in the art will understand that the apparatuses and methods specifically described herein and illustrated in the accompanying drawings are non-limiting example embodiments and that the scope of the various embodiments of the present disclosure is defined solely by the claims. The features illustrated or described in connection with one example embodiment may be combined with the features of other example embodiments. Such modifications and variations are intended to be included within the scope of the present disclosure.

According to one embodiment, a volatile composition dispenser can be used to dispense at least one volatile composition and/or other solution or composition, such as a perfume, a fragrance, and/or an insecticide, for example, to an area or atmosphere surrounding the volatile composition dispenser. The volatile composition can comprise a single chemical or a single material that is capable of entering the vapor phase under atmospheric conditions or, more commonly, the volatile composition can comprise a mixture of chemicals and/or materials that are capable of entering the vapor phase under atmospheric conditions.

In one embodiment, the volatile composition can comprise, but is not limited to, a substance that can function as an air freshener, a deodorant, an odor neutralizing material, an odor blocking material, a malodor counteractant, an odor masking material, an aromatherapy material, an aromachology material, an insecticide, and/or a combination thereof. In other various embodiments, the volatile composition can comprise other various materials that can act in their vapor phase to modify, enhance, and/or treat an atmosphere or an area outside of the volatile composition dispenser.

For purposes of illustration, but without intending to limit the scope of the disclosure, the disclosure will be described as an air freshening system for delivering a liquid containing a volatile composition, such as a perfume or a fragrance, for example. In one example embodiment, the volatile composition dispenser can be configured to be used within an interior space or passenger compartment of a vehicle, for example, although the present disclosure is not limited to such use. While the volatile composition dispenser will be discussed herein with reference to use within a vehicle, those of skill in the art will understand that the dispenser can be configured for use in any environment, such as a home or an office, or can even be worn by a person, for example, and can be configured to dispense any suitable solution, chemical, material, and/or composition.

In various embodiments, a volatile composition dispensed by the dispenser and can comprise any suitable solution, chemical, material, and/or composition configured to make the interior space or passenger compartment of the vehicle smell more pleasant to passengers and/or provide passengers with a good open door experience when entering the vehicle, for example, by either evaporating a pleasant fragrance and/or by evaporating a composition that can neutralize and/or at least partially eliminate malodors.

The present disclosure generally relates to a non-energized volatile composition dispenser for the delivery of a volatile composition in a continuous manner. "Non-energized" can mean that the apparatus is passive and does not require to be powered by a source of external energy. In particular, in one embodiment, the volatile composition dispenser does not need to be powered by a source of heat, gas, or electrical current, and the volatile composition is generally not delivered by aerosol means.

In various embodiments, the volatile composition dispenser can deliver the at least one volatile composition in a continuous, or substantially continuous, manner when the volatile composition dispenser is in a resting position (i.e., the volatile composition dispenser is not being moved relative to the vehicle). The emission level of the at least one volatile composition may exhibit a uniform intensity until all of, or substantially all of, the at least one volatile composition is exhausted from a volatile composition container of the volatile composition dispenser. The continuous emission of the at least one volatile composition can be of any suitable length, such as up to 20 days, 30 days, 60 days, 90 days, shorter or longer periods, or any period between 10 to 90 days, for example. Of course, more or less volatile composition can be provided in the volatile composition dispenser to increase or decrease its useful life. Also, the volatile composition dispenser's useful life may be dependant on the conditions (i.e., temperature, pressure, moisture content, etc.) in which it operates.

In one non-limiting embodiment, referring to FIG. 1, a volatile composition dispenser 10 is illustrated positioned on a vent 12 of an air handling system of a vehicle. The vent 12 can comprise a plurality of louvers 13 and a louver adjustment mechanism 15, for example. The volatile composition dispenser 10 can be attached to the vent 12 by engaging a mounting portion of the dispenser 10 with the louvers 13, for example. In such an embodiment, air being forced or blown out of the vent 12 by the air handling system can flow through the volatile composition dispenser 10 to deploy any evaporated (i.e., vapor phase) volatile composition from the volatile composition dispenser 10 to an interior space or passenger compartment of the vehicle. Such deployment of the volatile composition, as discussed above, can treat air within the passenger compartment or interior space of the vehicle, for example. Those of skill in the art will recognize that the volatile composition dispenser described herein can be a disposable, single-use item or can be replenished with a volatile composition or a volatile composition cartridge after the volatile composition has been at least mostly used.

In one non-limiting embodiment, referring to FIGS. 1-10, the volatile composition dispenser 10 can comprise an outer shell 14. The outer shell 14 can at least partially house the various internal components of the volatile composition dispenser 10. While the outer shell 14 is illustrated as being circular, it can also be square, rectangular, triangular, ovate, or any other suitable shape. In one embodiment, the outer shell 14 can also comprise various designs and/or colors, for example, to make the volatile composition dispenser 10 more aesthetically pleasing to a customer. In various embodiments, the outer shell 14 can be reusable while other various internal components (e.g., a volatile composition cartridge) of the volatile composition dispenser 10 can be replaced, for example. The outer shell 14 can be thermoformed, injection molded, and/or blow molded with any suitable material or materials. Suitable materials of the outer shell 14 can comprise plastics, such as Pentaplast Pentaform® 2101 available from Klockner, for example. In one embodiment, the material(s) of the outer shell 14 can comprise colored and/or non-colored, see-through plastic. The see-through material can permit observation of the amount of the volatile composition remaining in the volatile composition dispenser 10, which can be indicative of the end-of life of the volatile composition dispenser 10.

Figure 5:
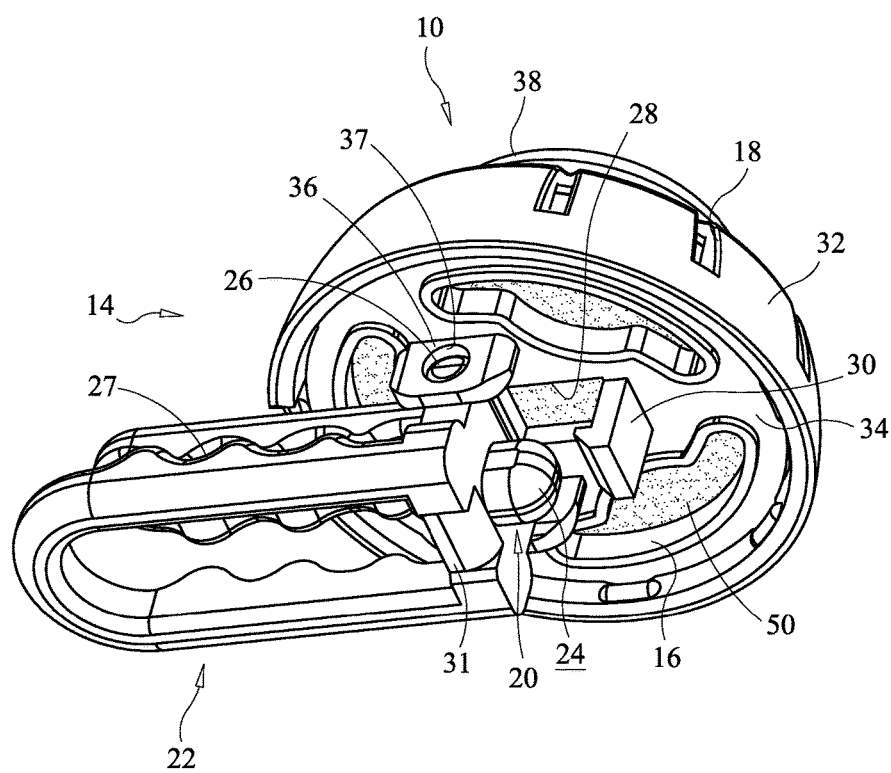
FIG. 5 is a bottom perspective view of the volatile composition dispenser of FIG. 2 in accordance with one non-limiting embodiment.
Figure 6:
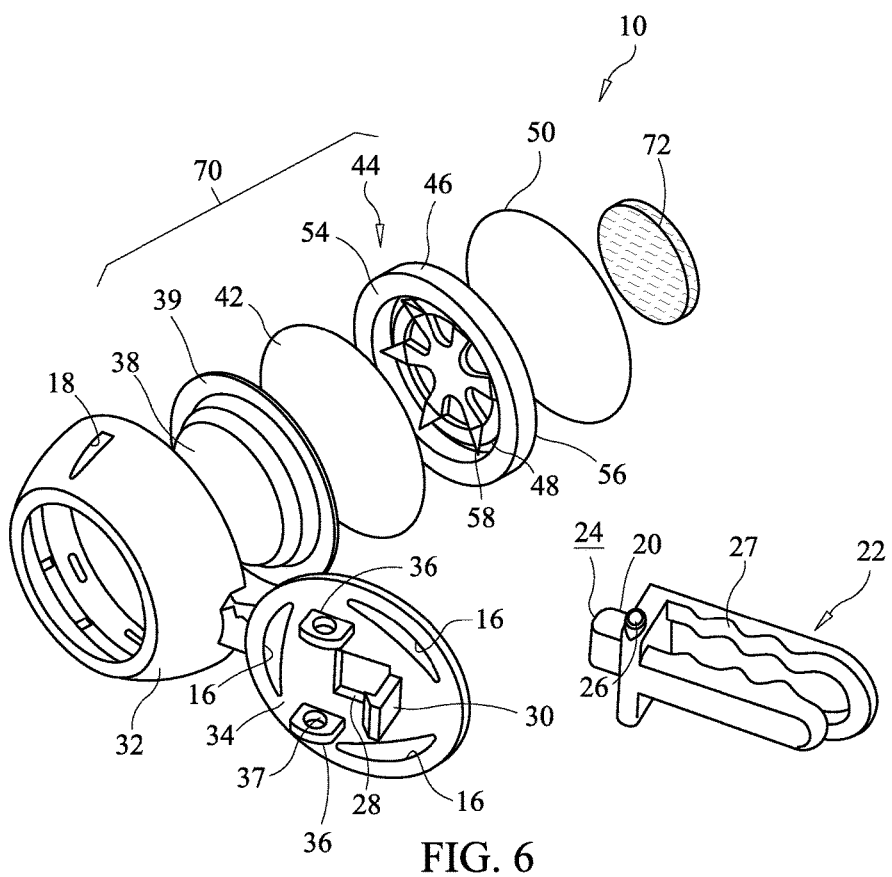
FIG. 6 is an exploded perspective view of various components of the volatile composition dispenser of FIG. 1 in accordance with one non-limiting embodiment.
Figure 7:
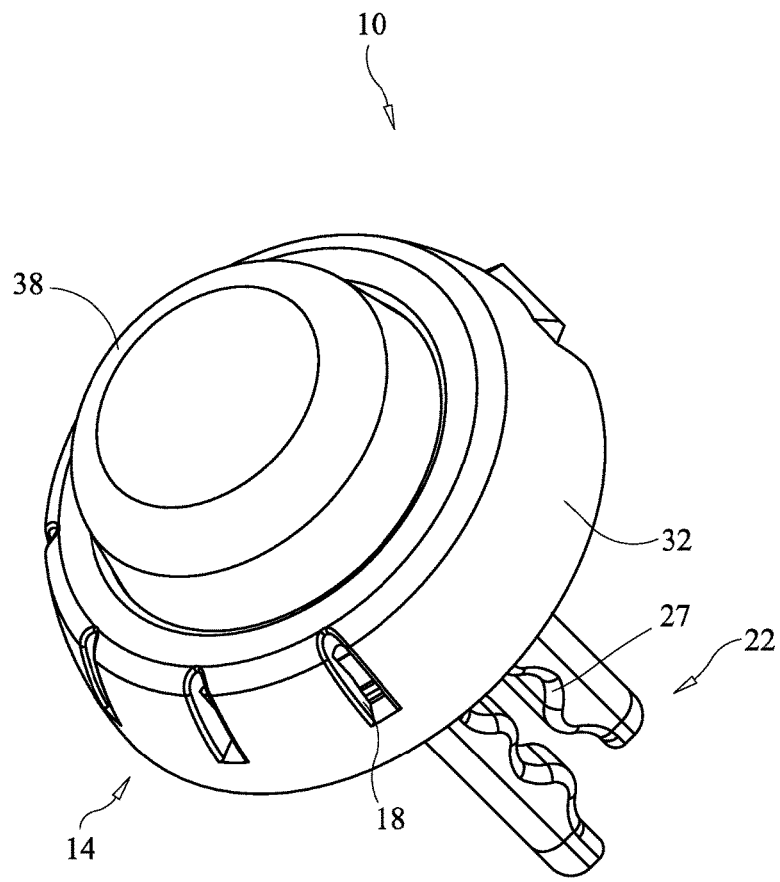
FIG. 7 is a top perspective view of the volatile composition dispenser of FIG. 2, with the cam in a second, actuated position in accordance with one non-limiting embodiment.
Figure 8:
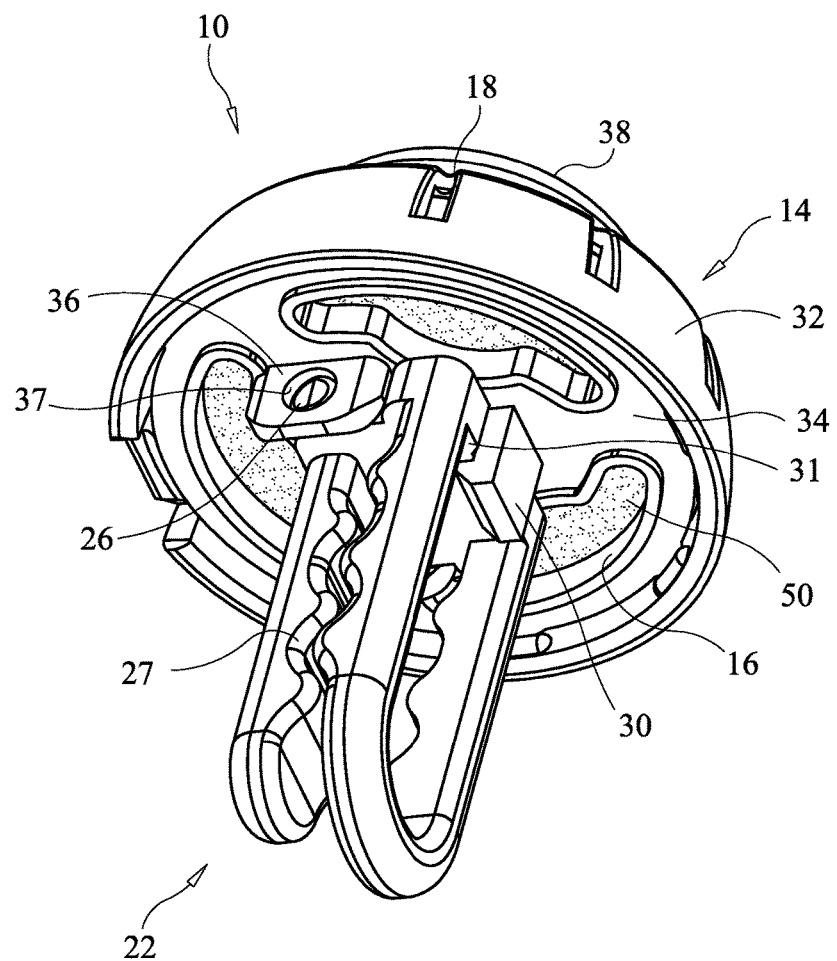
FIG. 8 is a bottom perspective view of the volatile composition dispenser of FIG. 2, with the cam in a second, actuated position in accordance with one non-limiting embodiment.
Figure 9:
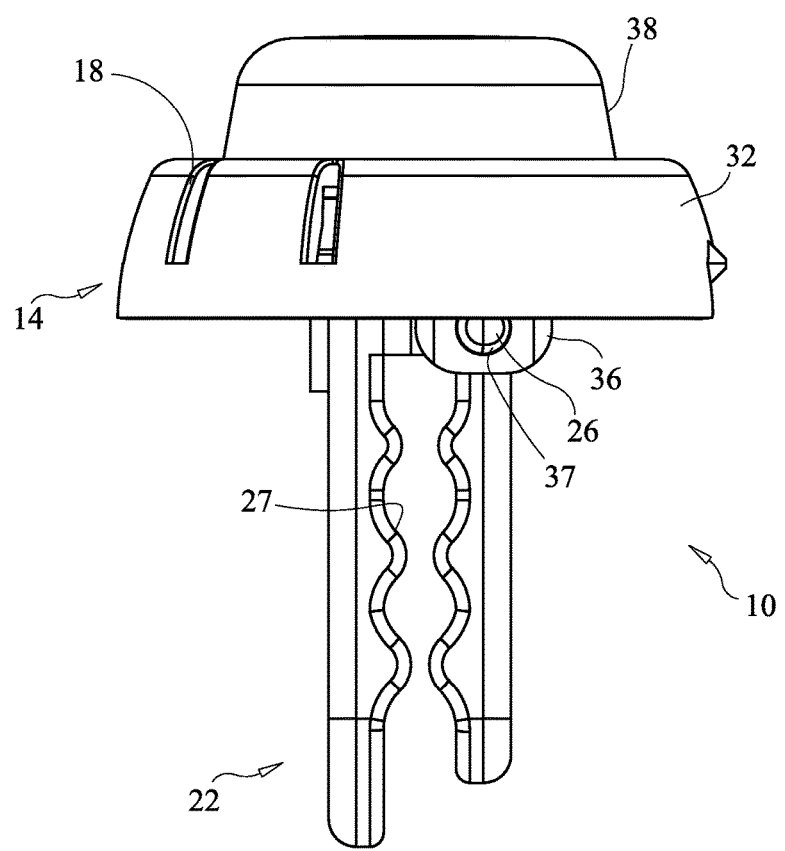
FIG. 9 is a side view of the volatile composition dispenser of FIG. 2, with the cam in a second, actuated position in accordance with one non-limiting embodiment.

In one non-limiting embodiment, referring to FIGS. 5, 6, and 8, the outer shell 14 can comprise at least one inlet vent 16 configured to allow air from an air system of a vehicle, for example, to enter the volatile composition dispenser 10. As the air from the air system enters the outer shell 14 of the volatile composition dispenser 10, it can be passed through or around a membrane, such as a breathable or a microporous membrane, for example. The membrane can be configured to receive the at least one volatile composition for evaporation. As the air passes through the membrane and/or internal portions of the outer shell 14, it can mix with the evaporated or partially evaporated volatile composition. In one embodiment, the mixture can then exit the volatile composition dispenser 10 and/or the outer shell 14 to treat the air surrounding the volatile composition dispenser 10. The at least one inlet vent 16 can comprise a plurality of inlet vents 16 having any suitable shape or orientation for allowing the air from the air system of the vehicle to enter the volatile composition dispenser 10 and mix with the evaporated or partially evaporated volatile composition.

In one non-limiting embodiment, referring to FIGS. 1, 2, and 4-9, the outer shell 14 can also comprise at least one optional outlet vent 18. The at least one outlet vent 18 can be in fluid communication, within the outer shell 14, with the at least one inlet vent 16 to allow any evaporated or partially evaporated volatile composition within the volatile composition dispenser 10 to exit the outer shell 14 and enter the passenger compartment or interior area of the vehicle. In various embodiments, the at least one outlet vent 18 can comprise a plurality of outlet vents 18 having any suitable shape or orientation for allowing the evaporated or partially evaporated volatile composition to exit the outer shell 14 of the volatile composition dispenser 10. In other embodiments, the volatile composition dispenser 10 can be positioned outside of a vehicle in an area with sufficient air flow such that air can flow through the volatile composition dispenser and dispense the evaporated or partially evaporated volatile composition to the atmosphere surrounding the volatile composition dispenser.

In one non-limiting embodiment, referring to FIGS. 2-10, the volatile composition dispenser 10 can also comprise a movable actuator or cam 20 (a "cam") attached to or formed with a mounting portion 22. The cam 20 can comprise a camming surface 24 or more than one camming surface. In an embodiment where more than one camming surface is provided, the various camming surfaces can extend different distances from the cam 20, for example, to allow the cam 20 to apply different forces to a rupture element of the volatile composition dispenser 10 based on which camming surface is contacting the rupture element at a particular time. The cam 20 or the camming surface 24 can have any suitable shape or orientation for applying a sufficient predetermined force to the rupture element of the volatile composition dispenser 10. The camming surface 24 does not need to contact the rupture element directly and, in fact, can usually first contact a membrane and push the membrane toward the rupture element.

In one embodiment, still referring to FIGS. 2-10, the mounting portion 22 can be attached to, movably attached to, rotatably attached to, or pivotably attached to the volatile composition dispenser 10 or the outer shell 14 by a pin 26 engaged with at least one lug 36 extending from the outer shell 14, for example, such that the mounting portion 22 can rotate, move, and/or pivot, about the pin 26, with respect to the outer shell 14. In one embodiment, an aperture 37 can be defined in the at least one lug 36, wherein the aperture can receive the pin 26. In other embodiments, the mounting portion 22 can comprise at least one projection extending therefrom. The at least one projection can be engaged with apertures in a mounting bracket (not illustrated) formed with or attached to the outer shell 14 to attach the mounting portion 22 to the outer shell 14. Further, the mounting portion 22 can be used to attach the volatile composition dispenser 10 to an object, such as a vent of air system of a vehicle, for example. As such, the mounting portion 22 can comprise a plurality of detents 27 configured to be engaged with portions of the vent of the air system. Of course, the mounting portion 22 can also comprise any other suitable gripping or engaging features that would allow attachment of the volatile composition dispenser 10 to another object or the vent of an air system.

In one non-limiting embodiment, again referring to FIGS. 2-10, the cam 20 can be movable between a first, non-actuated position and a second, actuated position. In one embodiment, the first, non-actuated position is illustrated in FIGS. 2-5, and the second, actuated position is illustrated in FIGS. 7-10. As can be seen with reference to the figures, a user can move, pivot, and/or rotate the mounting portion 22 about the pin 26, for example, to move the cam 20, between the first, non-actuated position (FIGS. 2-5) and the second, actuated position (FIGS. 7-10). As the cam 20 is moved, pivoted, and/or rotated by actuation of the mounting portion 22, the camming surface 24 and at least a portion of the cam 20 can enter a recess 28 (FIG. 5) in the outer shell 14 and at least partially enter an internal portion of the outer shell 14. The purpose of the camming surface 24 and/or at least a portion of the cam 20 entering the internal portion of outer shell 14 is to allow the camming surface 24 to apply a sufficient predetermined force to a rupture element within the outer shell 14 to cause the rupture element to pierce or puncture a volatile composition container comprising a volatile composition therein to release the volatile composition onto a membrane. In one embodiment, the rupture element or a movable portion of the rupture element can be displaced about 1 mm to about 4 mm when actuated by the cam 20 and/or the camming surface 24. Of course, in other embodiments, the rupture element or the movable portion of the rupture element can move any suitable distance when rupturing, piercing, or puncturing a wall of the volatile composition container and/or a rupturable seal of the volatile composition container. As a result of this movement, the volatile composition can be dispensed to, dripped onto, or flowed onto a membrane (or an optional wick and then to the membrane) of the volatile composition dispenser 10 for evaporation. The volatile composition container, the volatile composition, the rupture element, and the membrane are discussed in further detail below.

In one non-limiting embodiment, referring to FIGS. 2, 3, 5, 6, 8, and 10, as the mounting portion 22 is actuated and moves, pivots, and/or rotates the cam 20 into the second, actuated position, the mounting portion 22 can engage an optional catch 30 extending from a second or bottom portion of the outer shell 14. The catch 30 can be configured to engage a slot, groove, projection 31, aperture etc. on the mounting portion 22 to retain the mounting portion 22 in a position where the cam 20 is in the second, actuated position. The catch 30 can also prevent, inhibit, or at least minimize the chance that the mounting portion 22 will move, pivot, and/or rotate with respect to the outer shell 14 during use of the volatile composition dispenser 10.

Upon delivery of the volatile composition dispenser 10 to a consumer or user, the mounting portion 22 can be positioned such that the cam 20 and camming surface 24 are in the first, non-actuated position and do not apply a force to a rupture element or to an element having a puncturing or a piercing member (together referred to herein as "rupture element") within the volatile composition dispenser 10. In another embodiment, the mounting portion 22 can be positioned such that the cam 20 and camming surface 24 do not apply a sufficient predetermined force to the rupture element to puncture or pierce the volatile composition container or a rupturable seal or wall on or attached to the volatile composition container, for example. As such, the volatile composition container can remain unpunctured or unpierced, thereby preventing, inhibiting, or at least reducing the chance that the volatile composition will evaporate and/or exit the volatile composition container prior to use by the consumer and/or prior to movement of the cam 20 into the second, actuated position.

In one non-limiting embodiment, referring to FIG. 6, an exploded perspective view of various components of the volatile composition dispenser 10 are illustrated. As illustrated, the outer shell 14 can comprise a first portion 32 comprising the at least one outlet vent 18 and a second portion 34 comprising the at least one inlet vent 16. Those of skill in the art will recognize that at least portions of the outer shell 14 can be eliminated, for example part of the second portion 34, and the volatile composition dispenser 10 can still function properly. In one embodiment, the first portion 32 of the outer shell 14 can be pivotably attached to, snap fit to, press fit to, or otherwise configured to engage or attach to the second portion 34. The mounting portion 22 can be attached to at least one lug 36 on the second portion 34, using the pin 26, to allow the mounting portion 22 to move, pivot, and/or rotate with respect to the second portion 34. If the first portion 32 of the outer shell 14 is pivotably or rotatably attached to the second portion 34 of the outer shell 14, the two portions 32 and 34 can be connected by a hinge, for example, or by another suitable rotatable or pivotable member.

In one non-limiting embodiment, still referring to FIG. 6, other various components of the volatile composition dispenser 10 can comprise a volatile composition container 38 configured to contain at least one volatile composition 40 therein (not illustrated in FIG. 6) and an optional rupturable seal 42 configured to cover a portion of the volatile composition container 38 to maintain at least most of the volatile composition 40 within the volatile composition container 38. The volatile composition container 38 can be comprised of a rigid or a flexible material. The volatile composition dispenser 10 can further comprise a rupture element 44 comprising an outer housing 46 and a movable portion 48 positioned at least partially within the outer housing 46. In addition, the volatile composition dispenser 10 can also comprise a membrane 50, such as a breathable membrane or a microporous membrane, for example. At least some of these various components can be at least partially positioned within the outer shell 14 and can be sealably engaged to each other using adhesive sealing, heat sealing, induction sealing, pressure sealing, ultrasonic bonding, crimping, and/or any other suitable sealing method or sealing compound, for example. The various components can be sealed together to allow the volatile composition 40 to exit or flow from the volatile composition container 38 when a puncturable, a piercable, and/or a rupturable wall (not illustrated) of the volatile composition container 38 and/or the rupturable seal 42 is punctured or pierced by the rupture element 44, such that the volatile composition 40 can be received on the membrane 50 for evaporation without leaking from the membrane 50 and without leaking between the seals of the components of the volatile composition dispenser 10. In one embodiment, the rupturable seal 42 may not be provided and the rupture element 44 can puncture or pierce a wall or other portion (hereafter the "wall") of the volatile composition container 38. Of course, in one embodiment, both the wall and the rupturable seal 42 can be punctured or pierced by the rupture element 44. The rupture element 44 can be injection, compression, or pressure molded using a polyolefin, such as polyethylene (PE) or polypropylene (PP), polyester, or other plastics known to be suitable for molding. In one embodiment, the rupture element 44 can also be made by thermoforming with a discrete cutting step to remove parts not wanted or required.

Further to the above, in one non-limiting embodiment, still referring to FIG. 6, the wall can be configured to at least partially maintain the volatile composition 40 within the volatile composition container 38 to prevent, inhibit, or at least reduce evaporation of the volatile composition 40 until it is released onto the membrane 50. The wall can be configured to be punctured, pierced, and/or ruptured by the rupture element 44. In other embodiments, the volatile composition container 38 can comprise one open side optionally comprising a flange 39 configured to be sealably or otherwise engaged with the rupturable seal 42. The rupturable seal 42 can be sealed to or engaged with the flange 39 by a layer of adhesives, heat, and/or pressure sealing, ultrasonic bonding, crimping, and the like or a combination thereof. In such an embodiment, the rupturable seal 42 can at least partially maintain the volatile composition 40 within the volatile composition container 38 to prevent, inhibit, or at least reduce evaporation of the volatile composition 40 until it is released onto the membrane 50. The rupturable seal 42 can be attached to the optional flange 39 of the volatile composition container 38 using adhesives, heat, pressure sealing, ultrasonic bonding, crimping, and/or other suitable sealing methods. In other embodiments, the rupturable seal 42 can be integrally formed with the volatile composition container 38, for example. In one embodiment, the rupturable seal 42 can comprise a rupturable substrate, such as a flexible foil, for example.

Further to the above, in one non-limiting embodiment, the rupturable seal 42 can be comprised of any material that ruptures or breaks upon the application of a sufficient force or a predetermined force, with or without the presence of an element to aid in such rupture. Because the rupturable seal 42 is intended to contain the volatile composition 40 within the volatile composition container 38 while the volatile composition container 38 or the volatile composition dispenser 10 is being stored, the rupturable seal 42 can be made from any barrier material that prevents or at least minimizes evaporation of the volatile composition 40 prior to use. Such materials can be impermeable, or at least substantially impermeable, to vapors and liquids. Suitable barrier materials for the rupturable seal 42 can comprise a flexible film, such as a polymeric film, a flexible foil, and/or a composite material, such as foil/polymeric film laminate, for example. Suitable flexible foils include a metal foil such as a foil comprised of a nitrocellulose protective lacquer, a 20 micron aluminum foil, a polyurethane primer, and 15 g/m2 polyethylene coating (Lidfoil 118-0092), available from Alcan Packaging. Alternative compositions of the rupturable seal 42 can comprise PE coating/Al Foil/PE coating or PP film/Al Foil/PE coating. In the event that the rupture element 44 is comprised of PP, then it can be sealed to a PP side of the rupturable seal 42, for example. In the event that the rupture element 44 is comprised of high-density polyethylene (HDPE), then the PE coating on the rupturable seal 42 can be HDPE to aid in heat sealing the rupture element 44 to the rupturable seal 42, for example. In any event, it can be preferable to have a heat seal coating on the rupturable seal 42 that will easily seal to any component (e.g., the rupture element 44 or the volatile composition container 38) to which the rupturable seal 42 is being attached (e.g., PE to PE, PP to PP, and HDPE to HDPE). In one embodiment, suitable polymeric films can comprise polyethylene terephtalate films (PET), acrylonitrile copolymer barrier films such as those sold under the trademark Barex® by INOES, ethylene vinyl alcohol, and combinations thereof. It is also contemplated that coated barrier films can be utilized as the rupturable seal 42. Such coated barrier films can comprise metalized polyethylene terephtalate (PET), metalized polypropylene, silica, and/or an alumina coated film. Any barrier material, whether coated or uncoated, can be used either alone and/or in combination with other barrier materials.

In one embodiment, the volatile composition container 38 can comprise about 0.5 ml to about 8 ml of liquid and/or gel containing or comprising the volatile composition 40. In other embodiments, the volatile composition container 38 can comprise about 1 ml to about 6 ml, about 1 ml to about 4 ml, about 2 ml, or about 4 ml, for example. Of course, any other suitable volume of the volatile composition 40 is within the scope of the present disclosure and can be used with the volatile composition container 38. In one embodiment, the volatile composition container 38 can comprise two or more volatile composition containers, each container having a different volatile composition, material, and/or chemical therein. Each of the volatile composition containers can be punctured by one or more rupture elements, for example. In other embodiments, the volatile composition container can comprise a single volatile composition container but the container can have two or more chambers, each chamber containing a different volatile composition, material, and/or chemical, for example. In various embodiments, where more than one volatile composition, chemical, and/or material is provided, the volatile compositions, materials and/or chemicals can be configured to mix with each when or after the rupture element is activated.

In one non-limiting embodiment, the rupture element 44 can be configured in any fashion or orientation such that a user can manually breach the rupturable seal 42 or the wall with relative ease using the mounting portion 22. In various embodiments, a first side or surface 54 of the outer housing 46 of the rupture element 44 can be sealably engaged with an outer portion of one of the wall and the rupturable seal 42 such that the movable portion 48 of the rupture element 44 can engage either the wall or the rupturable seal 42 to pierce, puncture, and/or rupture the wall or the rupturable seal 42 and thereby allow the release of the volatile composition 40 from the volatile composition container 38. The second side or surface 56 of the outer housing 46 can be sealably engaged with the membrane 50 using the various sealing techniques described herein (e.g., heat sealing, ultrasonic sealing, adhesive sealing, etc.).

As referenced above, again referring to FIG. 6, the movable portion 48 of the rupture element 44 can be attached to the outer housing 46, releasably attached to the outer housing 46, and/or merely positioned within the outer housing 46, but not attached thereto. In one embodiment, the movable portion 48 can be attached to the outer housing 46 via at least one biasing member 60, as will be discussed in further detail below. The movable portion 48 can comprise at least one or a plurality of puncturing members 58 positioned proximate to an outer perimeter of the movable portion 48 and/or in any other suitable position on the movable portion 48. Tips 62 of the puncturing members 58 and/or the puncturing members 58 themselves can be configured to puncture, rupture, or pierce an aperture or crack in one of the wall and the rupturable seal 42 to allow the volatile composition 40 to be released onto the membrane 50 for evaporation. In one embodiment, the outer housing 46 can comprise an annular lip (not illustrated) extending inwardly toward the movable portion 48. In such an embodiment, the movable portion 48 may not be attached to the outer housing 46. A portion of the movable portion 48 proximate to its outer perimeter can engage the lip, upon force applied to the movable portion 48, to prevent, inhibit, or at least minimize the chance that the entire movable portion 48 will be forced through the rupturable seal 42 or the wall. Instead, only the at least one puncturing member 58 or the tip 62 of the at least one puncturing member 58 may pierce the rupturable seal 42 and/or the wall.

In one non-limiting embodiment, still referring to FIG. 6, a plurality of puncturing members 58 can be positioned around the outer perimeter of the movable portion 48 such that no matter what orientation the volatile composition dispenser 10 is in, the lowermost portion of the wall or the rupturable seal 42 can be punctured, optionally in addition to other punctures in the wall or the rupturable seal 42 to allow the volatile composition 40 to easily flow out of the volatile composition container 38. In one embodiment, the volatile composition container 38 can comprise an uppermost portion and a lowermost portion, in any orientation of the volatile composition container 38. The puncture in the wall or in the rupturable seal 42 can be located proximate to the lowermost portion to allow the most volatile composition 40 to flow out of the volatile composition container 38. In various embodiments, between two and ten puncturing members 58 can be positioned proximate to an outer perimeter of the movable portion 48, alternatively between four and eight, alternatively six, and alternatively four, for example. By providing multiple puncturing members 58 positioned about, or proximate to, the outer perimeter of the movable portion 48, at least one of the puncturing members 58 can puncture the wall or the rupturable seal 42 at a lowermost point or substantially a lowermost point with respect to an uppermost portion of the volatile composition container 38. As such, at least most of the liquid volatile composition 40 within the volatile composition container can exit the volatile composition container 38 owing to the gravitational forces acting on the liquid volatile composition 40. In other embodiments, depending on the orientation of the volatile composition container 38, other suitable puncturing areas of the wall or the rupturable seal 42 may be appropriate. For example, in one embodiment, a middle portion of the wall or the rupturable seal 42 can be punctured.

Suitable predetermined forces applied to breach, rupture, pierce, and/or puncture the wall or the rupturable seal 42 may be less than about 100N, alternatively less than about 60N, alternatively less than about 50N, alternatively less than about 25N, alternatively between about 15N and about 25N, alternatively about 20N, alternatively less than about 15N, and alternatively less than about 10N, for example. Those of ordinary skill in the art will appreciate that the predetermined forces may vary depending on the physical properties and placement of the membrane 50, the rupture element 44, the number and design of the puncturing members 58, and/or the composition and/or thickness of the rupturable seal 42 or wall within the outer shell 14 of the volatile composition dispenser 10, for example.

Figure 10:
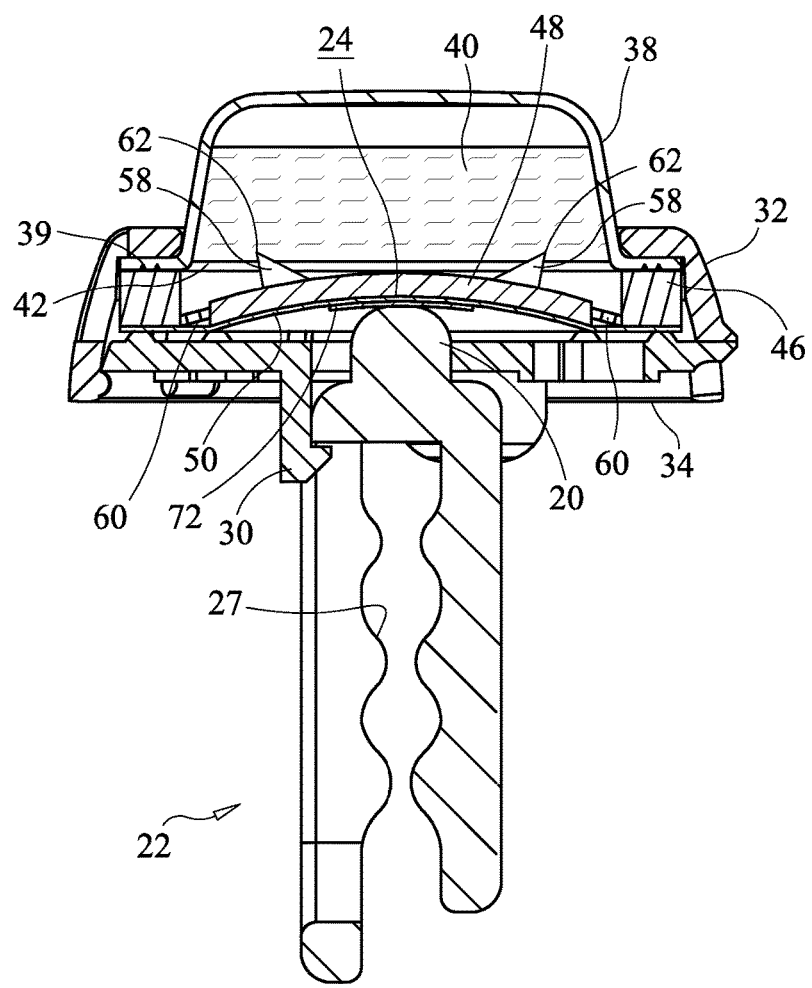
FIG. 10 is a cross-sectional view of the volatile composition dispenser of FIG. 9 in accordance with one non-limiting embodiment.

In one method of operation of the volatile composition dispenser 10, referring to FIG. 10, when the cam 20 is moved from the first, non-activated position into the second, activated position, the camming surface 24 of the cam 20 can be positioned at least partially through the recess 28 in the second portion 34 of the outer shell 14 and can first contact the membrane 50 and push it toward the rupture element 44. The movable portion 48 of the rupture element 44 can then move relative the outer housing 46 such that the puncturing members 58 can engage the wall or the rupturable seal 42 of the volatile composition container 38 and thereby puncture or pierce the wall or the rupturable seal 42 to release the volatile composition 40 onto the membrane 50 or a wick in contact with the membrane 50, for example. As such, the membrane 50 can be resilient and flexible enough to move when pushed by the camming surface 24 without breaching. In one embodiment, the camming surface 24 can move the rupture element 44 between about 1 mm and about 4 mm, for example. In one embodiment, the outer housing 46 of the rupture element 44 can be eliminated and the rupture element 44 can comprise the movable portion 48, for example.

In one embodiment, the membrane 50 can comprise breathable or microporous portions (i.e., portions through which air or another gas can flow). The breathable membrane 50 can be air or vapor permeable, yet can prevent, inhibit, or at least minimize the free flow of liquid or gel out of or through the membrane 50, thus addressing leakage issues. A microporous membrane includes the characteristics of a breathable membrane and is also capable of wicking liquid. Further, a microporous membrane can enable the diffusion of the at least one volatile composition 40 to be controlled by evaporation of the liquid volatile composition 40 versus being dependent on the diffusion rates of the volatile composition 40 through a polymer. Because the membrane 50 is shielded from the volatile composition 40 until the wall or the rupturable seal 42 is breached or punctured, the evaporated volatile composition or fragrance intensity can build slowly from zero to its equilibrium rate of release when the membrane 50 is fully wetted by the liquid volatile composition 40.

In one embodiment, the membrane 50 can have limited selectivity leaving behind less volatile composition, such as perfume or fragrance materials. Membranes that are selective, such as traditional polyethylenes, can inhibit high molecular weight volatile compositions and compositions with low solubility in polyethylene from diffusing therethrough. This can limit perfume formulations, for example in the field of air fresheners where it is typically desired to use formulations having a wide variety of volatile compositions having different volatilities. In one embodiment, for example, some membranes can preclude the diffusion of alcohols, such as linalool and dihydromyrcenol, for example, which are widely used in perfume applications.

While not wishing to be bound by any particular theory, the physical characteristics of the membrane 50 can affect the diffusion rate of the volatile composition 40 through the membrane 50. Such characteristics can include materials used, pore size, thickness, and evaporative surface area, for example.

The membrane 50, such as a microporous membrane, for example, can have an average pore size of about 0.01 microns to about 0.06 microns, alternatively from about 0.01 microns to about 0.05 microns, alternatively about 0.01 microns to about 0.04 microns, alternatively about 0.01 microns to about 0.03 microns, alternatively about 0.02 microns to about 0.04 microns, and alternatively about 0.02 microns, for example.

In one non-limiting embodiment, the membrane 50 can be filled with any suitable filler and plasticizer known in the art. The filler can comprise finely divided silica, clays, zeolites, carbonates, charcoals, and mixtures thereof. In various embodiments, the membrane 50 can be filled with about 50% to about 80%, by total weight, of silica, alternatively about 60% to about 80%, alternatively about 70% to about 80%, and alternatively about 70% to about 75%, for example. Further, in one embodiment, the membrane 50 can have a thickness of about 0.01 mm to about 1 mm, alternatively about 0.1 mm to about 0.4 mm, alternatively about 0.15 mm to about 0.35 mm, and alternatively about 0.25 mm, for example.

Those of ordinary skill in the art will appreciate that the surface area of the membrane 50 can vary depending on the user preferred size of the volatile composition dispenser 10 and/or the outer shell 14, for example. In some example embodiments, the evaporative surface area of the membrane 50 can be about 0.25 $cm^2$ to about 100 $cm^2$, alternatively about 0.25 $cm^2$ to about 50 $cm^2$, alternatively about 0.5 $cm^2$ to about 25 $cm^2$, alternatively about 0.5 $cm^2$ to about 10 $cm^2$, alternatively about 0.5 $cm^2$ to about 6 $cm^2$, and alternatively about 0.75 $cm^2$ to about 3 $cm^2$, for example.

Figure 3:
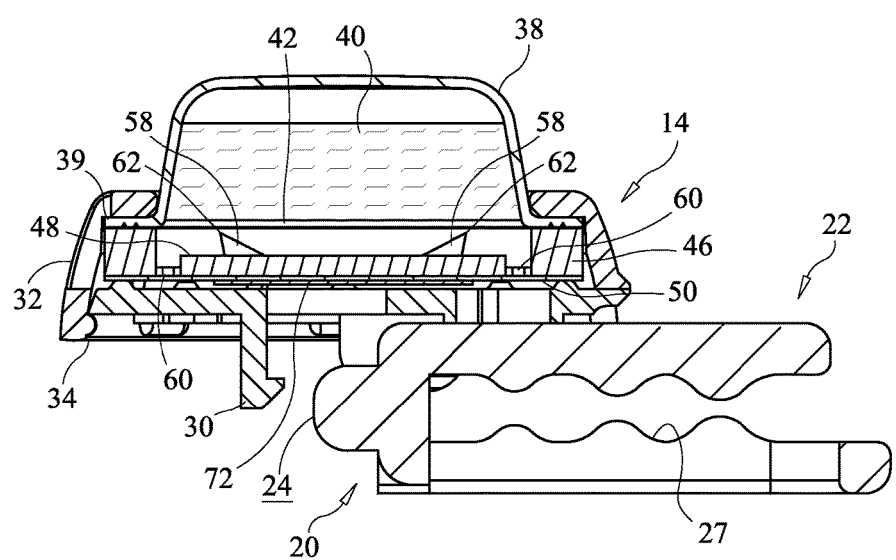
FIG. 3 is a cross-sectional view of the volatile composition dispenser of FIG. 2 in accordance with one non-limiting embodiment.
Figure 4:
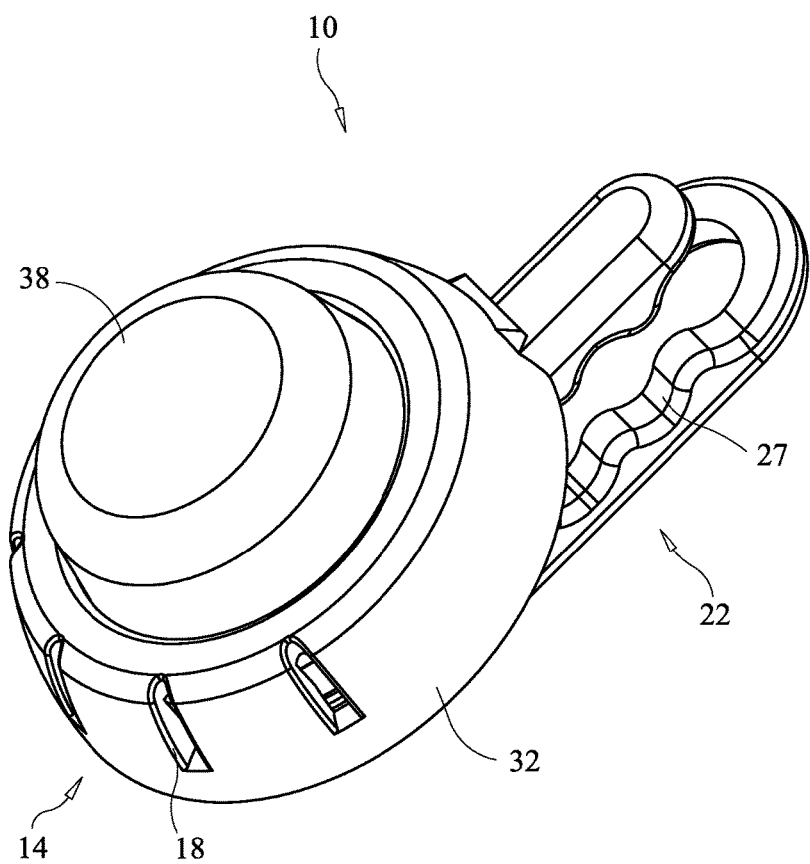
FIG. 4 is a top perspective view of the volatile composition dispenser of FIG. 2 in accordance with one non-limiting embodiment.

In one non-limiting embodiment, referring to FIGS. 3, 6, and 10, the evaporative surface area of the membrane 50 can be modified by sealing or otherwise attaching a barrier film 72 (i.e., a substantially non-gas or liquid permeable film, coating, and/or material) to a portion of the membrane 50 to reduce the evaporative surface area of the membrane 50 and provide a more controlled and/or slower evaporation of the volatile composition 40, for example. In one embodiment, the barrier film 72 can be positioned on the membrane 50 such that the camming surface 24 of the cam 20 can at least partially engage the barrier film 72 on the membrane 50 and not the membrane 50 itself, for example. Such engagement of the barrier film 72 by the camming surface 24 can prevent, inhibit, or at least minimize the risk that damage will be caused to the membrane 50 by the camming surface 24 when the camming surface 24 applies a predetermined force to the membrane 50. By providing the barrier film 72 on the membrane 50 at least where the camming surface 24 may engage the membrane 50, leakage of the membrane 50 can be prevented or at least minimized. In one example embodiment, the barrier film 72 can be comprised of a PET film with a PE heat seal coating, for example. The barrier film 72 can be die-cut to have about a 50% open area, for example, and a PE heat seal coating can be heat seal laminated to the membrane 50 to effectively reduce the evaporative surface area of the membrane 50 by about 50%, for example. In one embodiment, the barrier film 72 can comprise the same diameter or perimeter as the membrane 50 and can have apertures therein to reduce the evaporative surface area of the membrane 50. In other embodiments, the barrier film 72 can have a smaller diameter or perimeter than the membrane 50 and may or may not have apertures therein, thereby leaving a portion of the membrane 50 uncovered by the barrier film 72, for example. A barrier film, of course, can also be used with other embodiments and membranes of the present disclosure, although not specifically referenced therewith.

Suitable non-limiting membranes 50 can comprise microporous, ultra-high molecular weight polyethylene (UHMWPE) optionally filled with silica as described in U.S. Pat. No. 7,498,369. Such UHMWPE membranes can comprise Daramic™ V5, available from Daramic, Solupor®, available from DSM (Netherlands), and Teslin™ HD 1100, available from PPG Industries, and combinations thereof. It is believed that these membranes can allow the volatile composition 40 to freely dissipate, while containing the liquid volatile composition 40 within the volatile composition dispenser 10.

Other suitable membranes can comprise any permeable polymeric, thermoplastic, or thermoset material, including acetal, acrylic, cellulosic, fluoroplastic, polyamide, polyester, polyvinyl, polyolefin, styrenic, etc., alone, co-extruded, woven or non-woven, mixed or in combination with elastomers, rubber, solids, silicas, and combinations thereof. Also suitable are films that allow good diffusion of the volatile composition, such as polyurethane films, Hytrel™ available from Dupont, Lotryl™ available from Arkema, and low density polyethylene films, for example. In other embodiments, any other suitable porous or nonporous membrane or film can be used with the volatile composition dispenser 10.

In one non-limiting embodiment, the membrane 50 can comprise a dye that is sensitive to the amount of the volatile composition 40 that it is in contact with to indicate end-of-life. Alternatively, the membrane 50 can change to transparent when in contact with a fragrance or the volatile composition 40 to indicate diffusion is occurring. Other means for indicating end-of-life that are known in the art are contemplated within the scope of the present disclosure.

Figure 11:
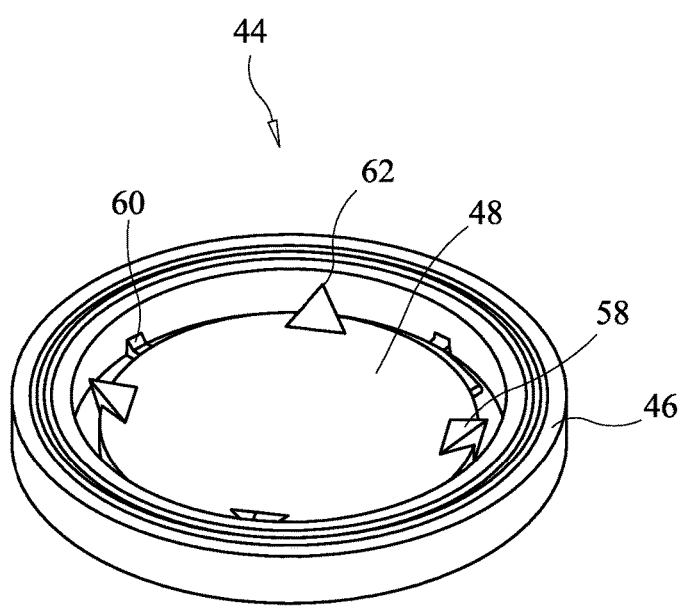
FIG. 11 is a top perspective view of a rupture element for a volatile composition dispenser in accordance with one non-limiting embodiment.
Figure 12:
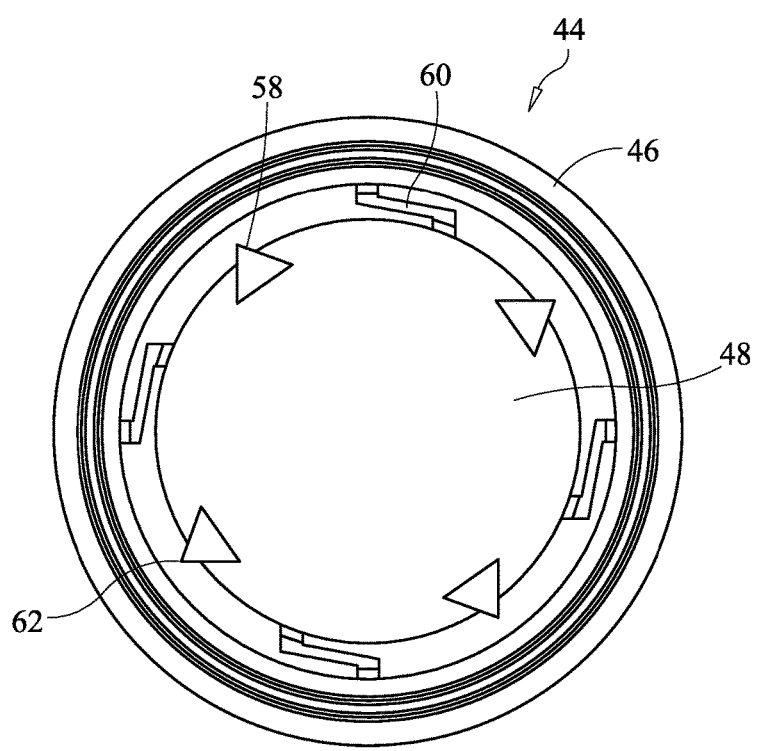
FIG. 12 is a top view of the rupture element of FIG. 11 in accordance with one non-limiting embodiment.

Further to the above, referring to FIGS. 10-12, an embodiment of the rupture element 44 is illustrated in further detail. The rupture element 44 can comprise the outer housing 46 and the movable portion 48 having the at least one puncturing member 58 positioned thereon. In one embodiment, the movable portion 48 can be attached to the outer housing 46 via the at least one biasing member 60 that can extend between the movable portion 48 and the outer housing 46. The at least one biasing member 60 can be configured to normally bias the movable portion 48, and the at least one puncturing member 58 positioned thereon, away from the wall or the rupturable seal 42 to prevent, inhibit, or at least reduce the chance that the puncturing member 58 will prematurely puncture or pierce the rupturable seal 42 or the wall potentially leading to premature evaporation of the volatile composition 40. In one embodiment, referring to FIG. 10, the at least one biasing member 60 can flex, bend, or stretch when the camming surface 24 applies a predetermined force to the movable portion 48. In another embodiment, the at least one biasing member 60 can comprise a frangible portion that can break when the camming surface 24 applies a predetermined force to the movable portion 48 to allow the movable portion 48 to move toward the rupturable seal 42 or the wall. Those of ordinary skill in the art will recognize that the at least one biasing member 60 can comprise springs, frangible elements or materials, elastic members, resilient members, plastic materials, resilient materials, flexible materials, elastic materials, and/or other suitable members or materials. As illustrated in FIG. 10, the movable portion 48 can also flex, stretch, or bend upwardly, optionally into an arcuate configuration, toward the rupturable seal 42 or the wall when the camming surface 24 applies the predetermined force thereto.

In one non-limiting embodiment, through the use of the at least one biasing member 60, at least one of the puncturing members 58 can be deployed into and at least partially through the rupturable seal 42 or the wall, when the predetermined force is applied to the movable portion 48 by the camming surface 24. Then, the at least one puncturing member 58 can be at least partially withdrawn from contact with the rupturable seal 42 or the wall, owing to the at least one biasing member 60, to allow the volatile composition 40 to flow through an aperture created in the rupturable seal 42 or the wall. In other embodiments, the cam 20, the camming surface 24, and/or the pivot of the mounting portion 22 (about the pin 26) can be configured such that the camming surface 24 applies a force to the membrane 50 and the rupture element 44 to cause at least a portion of the rupture element 44 to move about 1 mm to about 4 mm, for example, toward the rupturable seal 42 and puncture the rupturable seal 42. The camming surface 24 can then retract from contact with the membrane 50 such that the camming surface 24 no longer applies the predetermined force to the membrane 50 and the rupture element 44, as the camming surface 24 moves into the final activated, fully deployed, and/or latched position.

In one non-limiting embodiment, a collection basin (not illustrated) can be positioned proximate to the membrane 50 to collect the liquid or gel volatile composition 40 dispensed from the volatile composition container 38 prior to the liquid volatile composition 40 being received by the membrane 50. The collection basin can provide even, substantially even, and/or consistent distribution of the liquid or gel volatile composition 40 onto the membrane 50. Those of ordinary skill in the will recognize that the collection basin can have any suitable configuration and/or orientation which allows the liquid or gel volatile composition 40 to be evenly dispensed, at an appropriate flow rate, onto the membrane 50 for evaporation.

In one non-limiting embodiment, again referring to FIG. 6, a volatile composition cartridge 70 (illustrated in an exploded view) can be provided for use with the volatile composition dispenser 10 or other suitable volatile composition dispenser. In one example embodiment, the volatile composition cartridge 70 can comprise the volatile composition container 38 comprising the at least one volatile composition 40 therein. The volatile composition cartridge 70 can also comprise the rupture element 44, which can be positioned proximate to the volatile composition container 38 and sealably engaged with the volatile composition container 38. In another embodiment, the volatile composition cartridge 70 can further comprise a rupturable seal 42 or a foil sealably engaged with the volatile composition container 38. This rupturable seal 42 or foil can be breached, ruptured, pierced, or punctured by the rupture element 44 upon actuation of the rupturable element 44. Further, the volatile composition cartridge 70 can comprise the membrane 50 positioned proximate to the rupture element 44. The membrane 50 can be attached to an optional barrier layer 72, for example. In one embodiment, the rupture element 44 can be sealably engaged with a portion a portion of the membrane 50. As such, the rupture element 44, upon activation by the cam 20 of a volatile composition dispenser 10, can be configured to create an aperture in the volatile composition container 38 to release the volatile composition 40 from the volatile composition container 38 onto the membrane 50 for evaporation. Those of ordinary skill in the art will recognize that other embodiments of a volatile composition container, a rupturable seal, a rupture element, and a membrane can be included in the volatile composition cartridge 70 in lieu of or in addition to the various example components discussed above.

A user can replace the volatile composition cartridge 70 once it has reached the end of its useful life or when the user desires a different scent, fragrance etc. to be dispensed by a volatile composition dispenser. To replace the volatile composition cartridge 70, the user can open the outer shell 14 by rotating the second portion 34 away from the first portion 32, for example, or, in other embodiments, by otherwise separating (e.g., pulling apart) the first portion 32 of an outer shell 14 from the second portion 34 of the outer shell 14. The user can then insert a new volatile composition cartridge 70 into the outer shell 14 and then re-close the first portion 32 and the second portion 34 of the outer shell 14. In such a fashion, the user can reuse the outer shell 14, the mounting portion 22, and the cam 20, for example, and merely replace the volatile composition cartridge 70.

Figure 13:
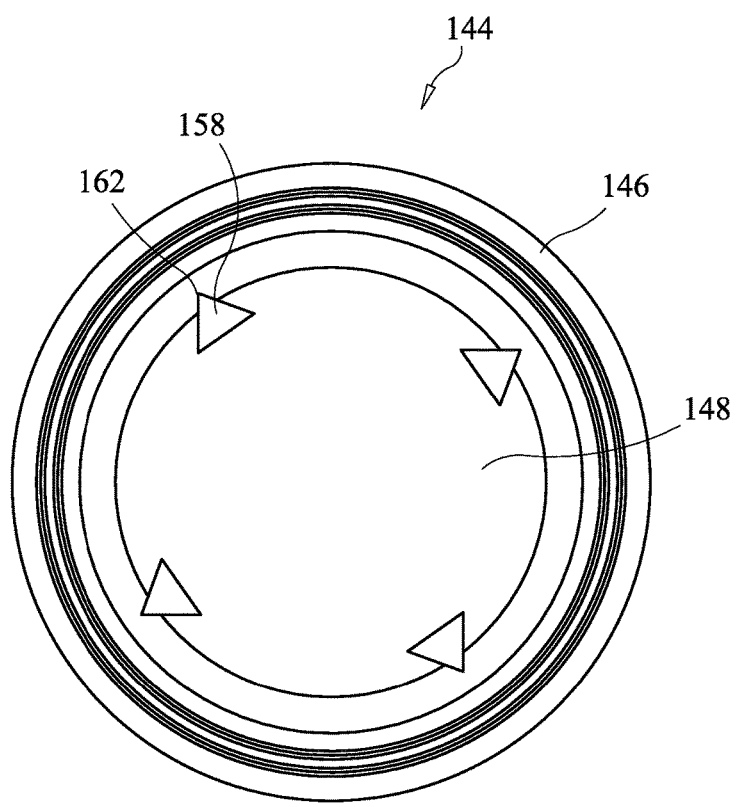
FIG. 13 is a top view of another rupture element for a volatile composition dispenser in accordance with one non-limiting embodiment.
Figure 14:
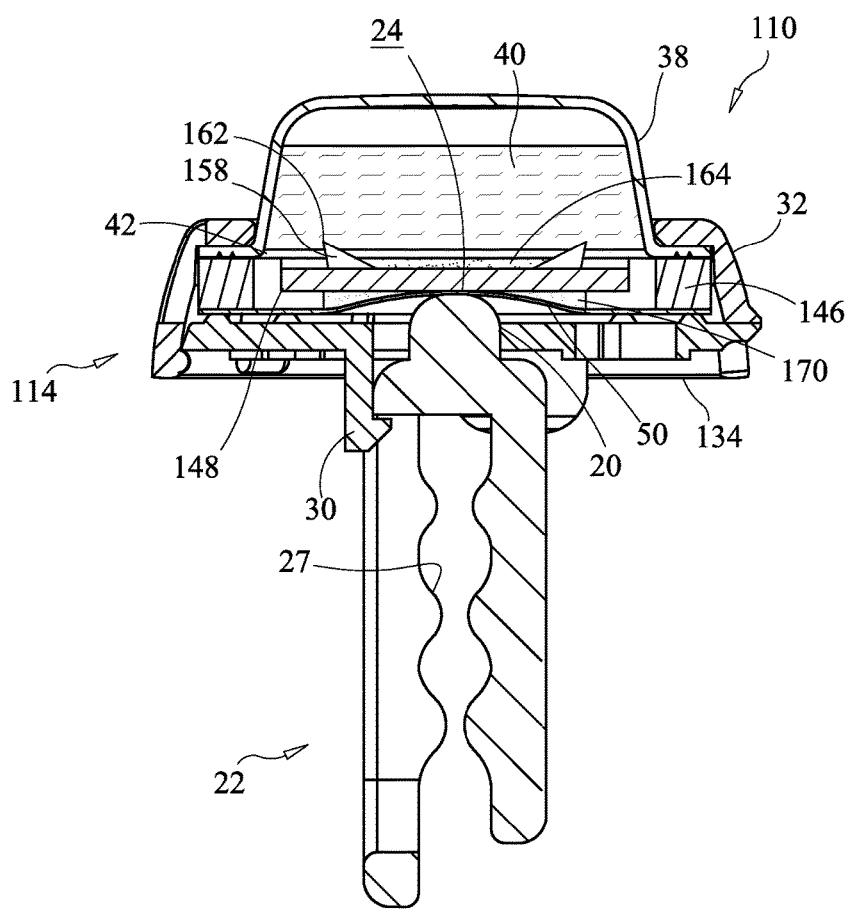
FIG. 14 is a cross-sectional view of a volatile composition dispenser using a deformable material and the rupture element of FIG. 13 in accordance with one non-limiting embodiment.
Figure 15:
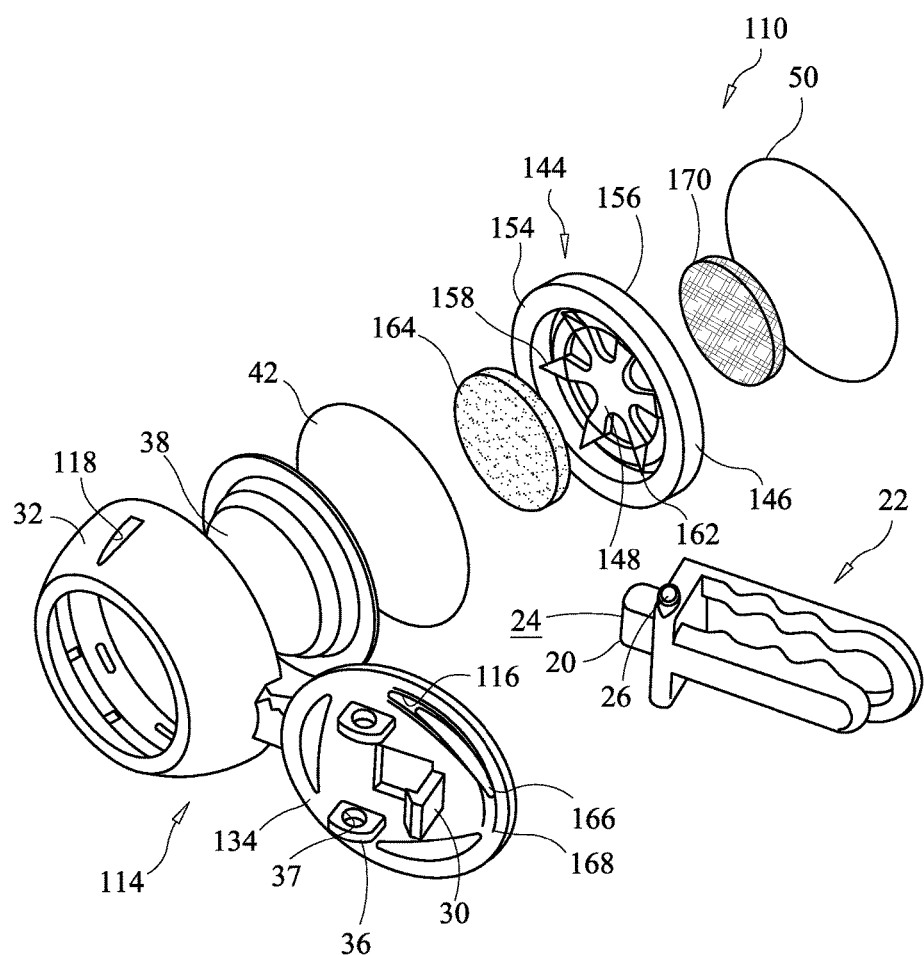
FIG. 15 is an exploded perspective view of various components of a volatile composition dispenser in accordance with one non-limiting embodiment.

In one non-limiting embodiment, referring to FIGS. 13-15, a volatile composition dispenser 110 can comprise a rupture element 144 comprising an outer housing 146 and a movable portion 148 having at least one puncturing member 158 thereon. The movable portion 148 can be positioned within the outer housing 146, but may not be attached to the outer housing 146. As such, the movable portion 148 can be essentially free floating within the outer housing 146. The outer housing 146 can comprise a first side or surface 154 configured for sealed attachment to the rupturable seal 42 or the wall and a second side of surface 156 configured for sealed attachment to the membrane 50. The sealing methods used in this embodiment can be the same as that described herein with respect to other embodiments In one embodiment, to prevent, inhibit, or at least minimize the chance that the at least one puncturing member 158 prematurely punctures the rupturable seal 42 or the wall of the volatile composition container 38, the at least one puncturing member 158 can comprise a blunt tip 162 configured to engage the rupturable seal 42. In such an embodiment, the blunt tip 162 may not puncture or pierce the rupturable seal 42 unless a sufficient predetermined force is applied by the camming surface 24, or other suitable actuator, to the movable portion 148. In other embodiments, a deformable or compressible material 164, such a polyolefin or polyurethane foam, for example, which can be deformed and/or compressed under a sufficient predetermined force, can be positioned intermediate the rupturable seal 42 or the wall and at least a portion of the movable portion 148 to normally bias the movable portion 148 away from the rupturable seal 42 or the wall, but still allow the at least one puncturing member 158 to puncture or pierce the rupturable seal 42 or the wall, optionally through the deformable or compressible material 164, when the camming surface 24 applies a sufficient predetermined force to the movable portion 148. The sufficient predetermined force can be in the force ranges described above or can include other force ranges. Of course, the deformable or compressible material 164 can be positioned intermediate part of the movable portion 148 and the rupturable seal 42 or the wall such that the at least one puncturing member 158 can puncture the rupturable seal 42 or the wall without needing to puncture through the deformable or compressible material 164, for example. It will be understood that the barrier film 72 described above, although not illustrated in FIGS. 13-15, can be used with the various embodiments of FIGS. 13-15 in the same manner as described above.

In one non-limiting embodiment, referring to FIG. 15, an exploded view of the volatile composition dispenser 110 is illustrated. The volatile composition dispenser 110 can comprise the volatile composition container 38 containing at least one volatile composition therein. The volatile composition dispenser 110 can also comprise the rupturable seal 42, the rupture element 144, the membrane 50, and an optional wick 170. The volatile composition dispenser 110 can also comprise an outer shell 114 having the first portion 32 and a second portion 134. Further, the volatile composition dispenser 110 can comprise the mounting portion 22 comprising the cam 20 comprising the camming surface 24. In one embodiment, referring to FIGS. 14 and 15, the deformable or compressible material 164, can be positioned at least partially intermediate the rupture element 144 and/or the movable portion 148 of the rupture element 144 and one of the wall of the volatile composition container 38 and the rupturable seal 42 to prevent, inhibit, or at least minimize the possibility that the movable portion 148 of the rupture element 144 will move toward one of the wall and the rupturable seal 42 and prematurely puncture the rupturable seal 42 or the wall. Unless otherwise indicated herein, the reference numerals corresponding to the reference numbers used above can be construed as being the same as, or substantially similar to, that described above.

In one non-limiting embodiment, referring to FIG. 15, an air flow adjustment member can be configured to be positioned over at least one vent of the volatile composition dispenser 110. In one embodiment, an air flow adjustment member 166 can be positioned on or formed with the second portion 134 of the outer shell 114. The air flow adjustment member 166 can be configured to move at least partially over or fully over at least one of the inlet vents 116 in the second portion 134. In one embodiment, the air flow adjustment member 166 can comprise two rails (not illustrated) extending therefrom, which can engage slots or tracks 168 in the second portion 134 of the outer shell 114. As a result, the air flow adjustment member 166 can slide or move along the tracks 168 from a first position, where it does not cover the at least one inlet vent 116, and a second position, where it at least partially covers at least a portion of the at least one inlet vent 116. In other embodiments, an air flow adjustment member can be configured to move between a first position, where it is free from covering all of the inlet and/or the outlet vents 116 and 118, and a second position, wherein it at least partially covers all of the inlet and/or outlet vents 116 and 118 on the volatile composition dispenser 110. Those of skill in the art will recognize that other suitable air flow adjustment members may be used with the present disclosure and that the air flow adjustment member 166 can be provided on each inlet vent 116 and/or each outlet vent 118, as required for appropriate air flow through the volatile composition dispenser 110.

By providing the air flow adjustment member 166 or other air flow adjustment member, a user can adjust the air flow rate through the volatile composition dispenser 110 and thereby adjust the amount of evaporated volatile composition dispensed by the volatile composition dispenser 110 to an atmosphere surrounding the volatile composition dispenser 110. This feature gives the consumer the ability to essentially "customize" the volatile composition dispenser 110 to various personal preferences. If all of the vents are uncovered, more air can flow through the volatile composition dispenser 110 thereby providing more fragrance, malodor treatment etc. to an atmosphere surrounding the volatile composition dispenser 110. If at least some of the vents are covered, less air can flow through the dispenser 110 thereby providing less fragrance, malodor treatments etc. to the atmosphere surrounding the volatile composition dispenser 110.

Figure 19:
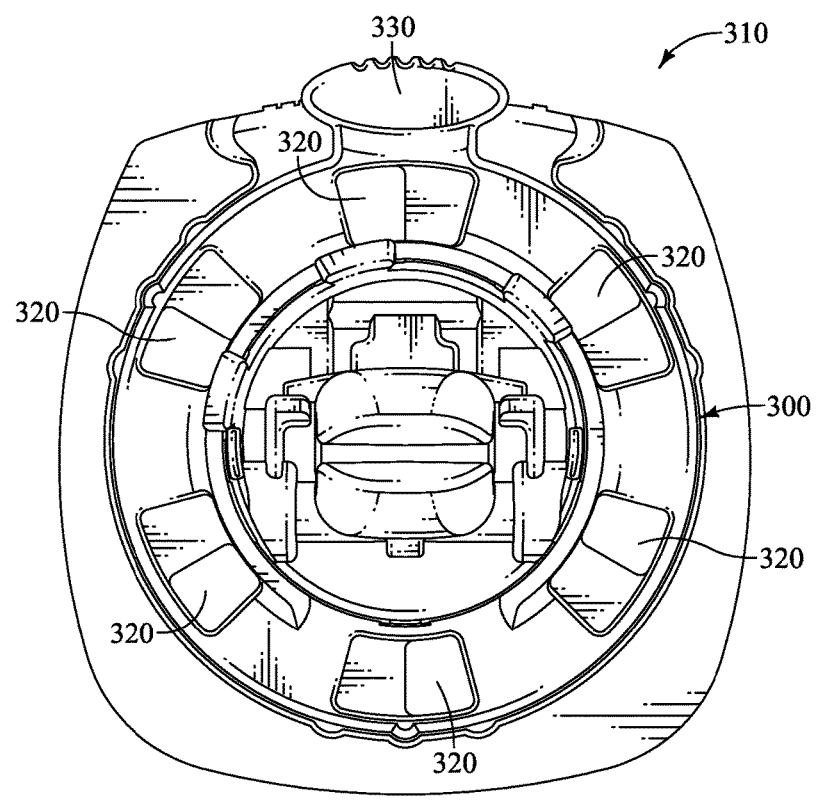
FIG. 19 is a rear view of a volatile composition dispenser in accordance with one non-limiting embodiment.

Referring to FIG. 19, another non-limiting embodiment of a volatile composition dispenser 310 having an air flow adjustment member is shown. The volatile composition dispenser 310 includes an intensity dial member 300 which allows a consumer to rotate dial member 300 by pressing on intensity dial element 330 which closes and opens evaporation apertures 320. The consumer has the ability to adjust the intensity dial element 330 so that the evaporation apertures 320 can be in the fully opened position, fully closed position, or any position therebetween. For instance when a consumer desires less fragrance release, evaporation apertures 320 could for example be in the fully closed position. Alternatively, if a consumer desires to maximize fragrance release, intensity dial member 300 can be rotated such that the evaporation apertures 320 are in the fully open position.

In one non-limiting embodiment, referring to FIGS. 14 and 15 (although applicable to other embodiments as well), the wick 170 can be provided between the rupture element 144 and the membrane 50 to facilitate the substantially constant wetting of the membrane 50. Another wick can also be provided in other suitable areas of the volatile composition dispensers described herein, such as between the rupture element 144 and the rupturable seal 42, for example. In one embodiment, the wick 170 can be smaller in diameter or perimeter than the membrane 50 such that it will not interfere with, or substantially interfere with, the seal between the membrane 50 and the rupture element 144. In various embodiments, a portion of the wick 170 can be in contact with the membrane 50 to aid in keeping the membrane 50 at least mostly wetted with the liquid volatile composition 40 from the time when the volatile composition 40 is first released from the volatile composition container 38 until the end of the volatile composition dispenser's useful life. As the wick 170 can be abutted against the membrane 50, the wick 170 can provide the membrane 50 with a constant supply of the volatile material 40. As a result of the wick 170, the evaporation of the volatile composition 40 from the membrane 50 can be at least somewhat constant and continuous throughout the volatile composition dispenser's useful lifespan. The wick 170 can be comprised of any suitable wick or wicking material known to those of skill in the art, such as a porous polyolefin plastic wick available from Porex and/or a fiber based polyolefin or polyester wick available from Filtrona, for example. Alternatively, in one embodiment, any thermoplastic spunbond nonwoven material with a basis weight between about 5 grams and about 100 grams available from Fiberweb could also be used. Those of ordinary skill in the art will recognize that other known wick configurations, materials, and/or orientations may also be used and are within the scope of the present disclosure. In other various embodiments, the membrane 50 can comprise a microporous material that can act as a wick owing to the small pore sizes of the microporous material. A Daramic™ V5 material, available from Daramic, is an example of a microporous material or membrane that can be used and can function in a similar fashion.

Figure 16:
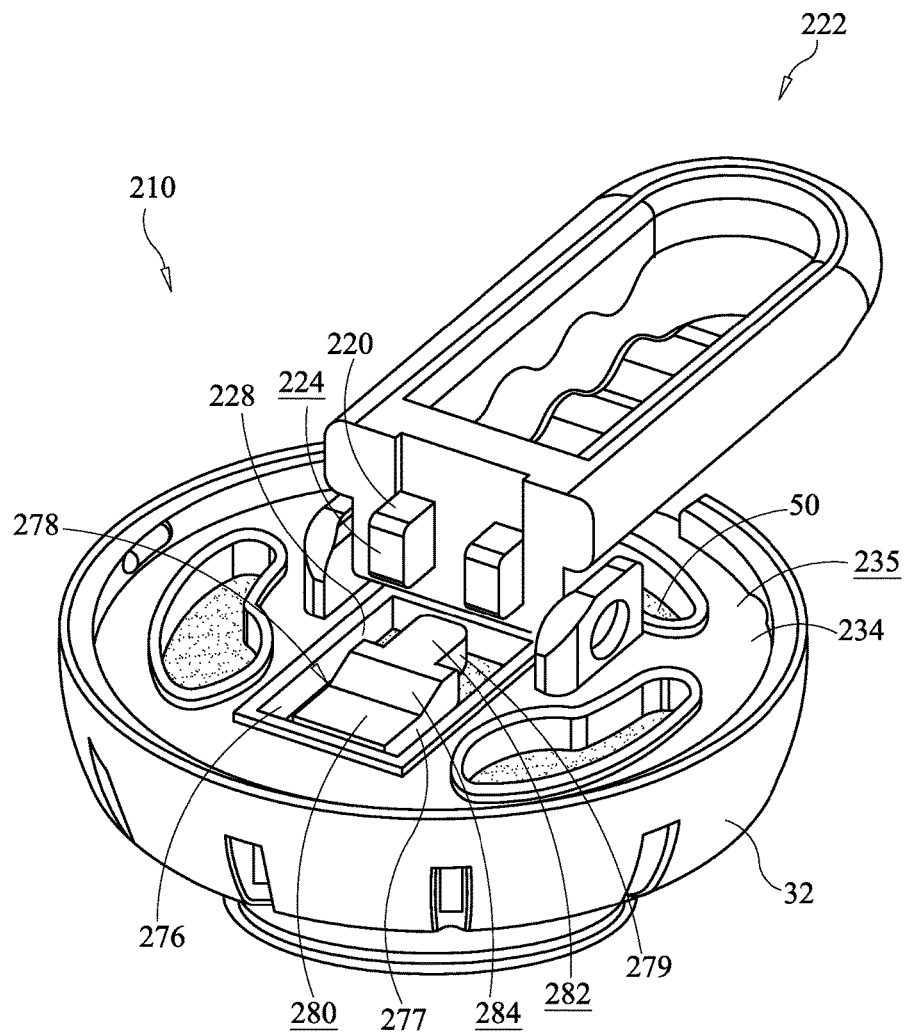
FIG. 16 is a bottom perspective view of another volatile composition dispenser with a cam in a non-actuated position in accordance with one non-limiting embodiment.
Figure 17:
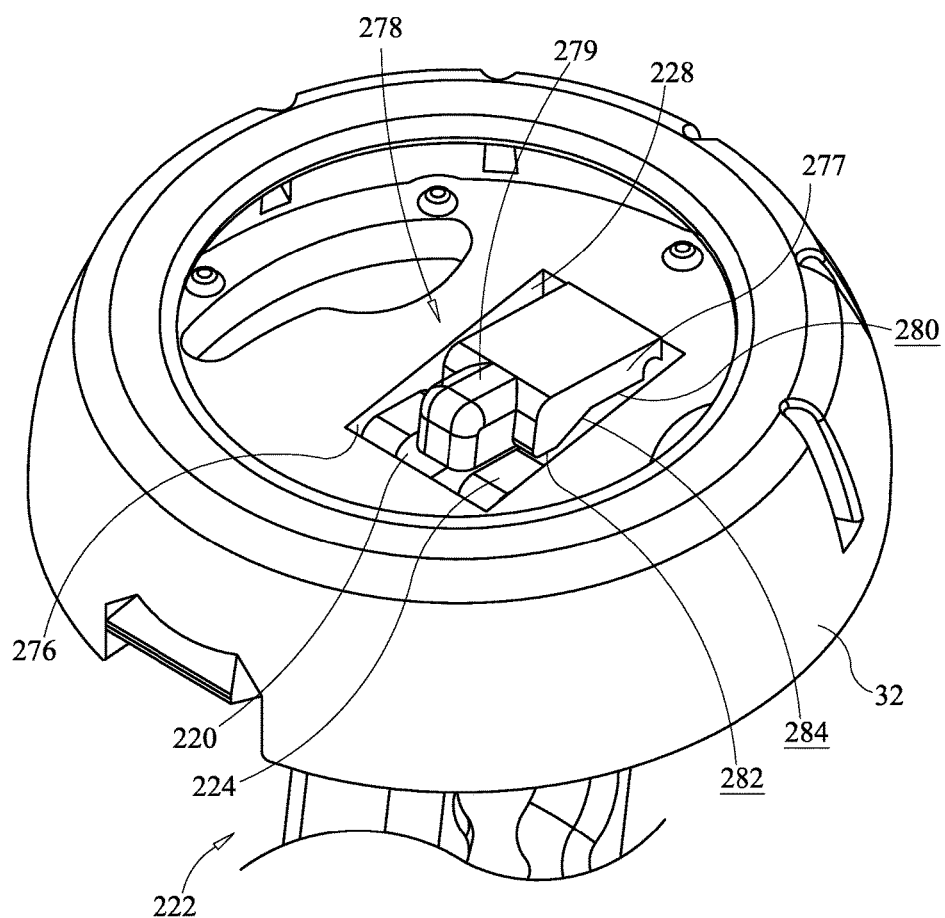
FIG. 17 is a top perspective view of a portion of the volatile composition dispenser of FIG. 16 with the cam in an intermediate position in accordance with one non-limiting embodiment.
Figure 18:
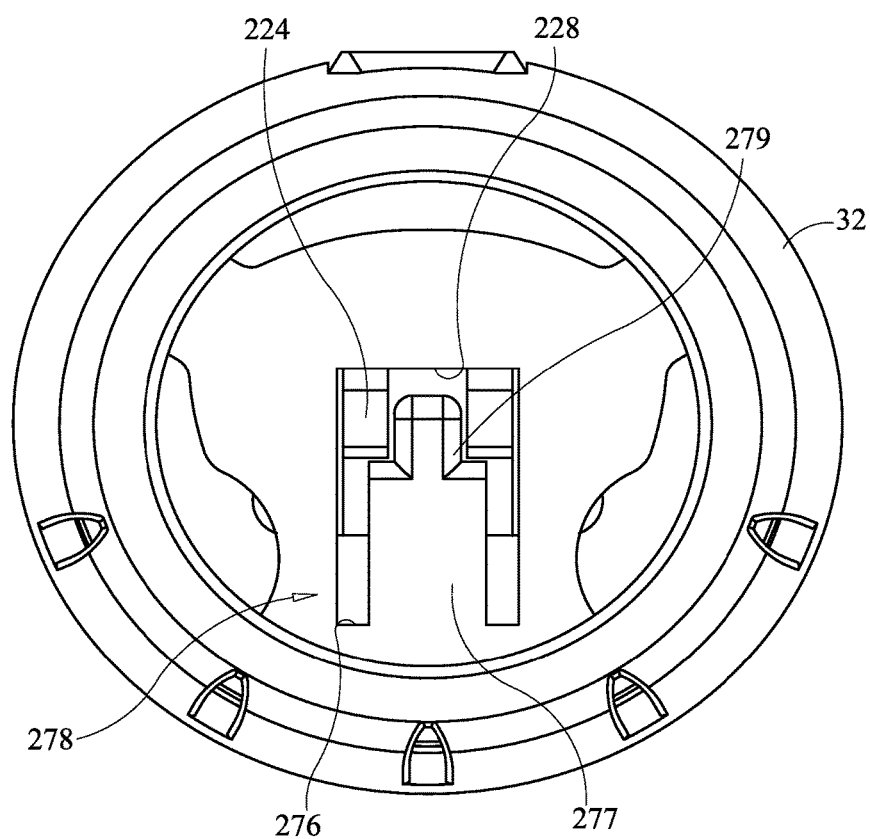
FIG. 18 is a top view of a portion of the volatile composition dispenser of FIG. 16 with the cam in a fully actuated position in accordance with one non-limiting embodiment.

Referring to FIGS. 16-18, a volatile composition dispenser 210 can comprise some or all of the various components of the volatile composition dispensers 10 and 110 discussed above. These various components can be arranged in the same or a similar fashion as described above. In one embodiment, however, the volatile composition dispenser 210 can comprise an outer shell 214 comprising a first portion 32 and a second portion 234. The second portion 234 can be somewhat similar to the second portions 34 and 134 above. In one embodiment, a recess 228 within the second portion 234 can comprise a side wall 276. A biasing member 278 can extend from a portion of the side wall 276 into the recess 228. The biasing member 278 can comprise a base portion 277 engaged with the side wall 276 and/or movably engaged with the side wall 276 and a projection portion 279 extending outwardly from the base portion 277 further into the recess 228. The projection portion 279 and/or the base portion 277 can comprise rounded or arcuate side walls or edges, for example, to at least reduce the possibility of damage being caused to the membrane 50 by the biasing member 278 upon contacting the membrane 50. An aperture can be defined between the side wall 276 of the recess 228 and the biasing member 278. The aperture can be large enough to receive at least a portion of at least one cam 220. In one embodiment, at least the projection portion 279 of the biasing member 278 can move with respect to a surface 235 of the second portion 234 when acted upon by at least one camming surface 224 of the at least one cam 220. In one embodiment, the biasing member 278 and/or the projection portion 279 can move between about 1 mm to about 4 mm, for example. Similar to that discussed above with respect to other embodiments, the at least one cam 220 can be attached to a mounting portion 222, wherein movement, pivoting, and/or rotating of the mounting portion 222 can move, pivot, and/or rotate the cam 220 between a first, non-actuated position and at least a second, actuated position.

Further to the above, in one non-limiting embodiment, the biasing member 278 can comprise a biasing surface comprising a first surface 280 on the base portion 277, a second surface 282 on the projection portion 279, and an intermediate surface 284 positioned at least partially between the first surface 280 and the second surface 282. The intermediate surface 284 can be positioned on at least one of the base portion 277 and the projection portion 279, as may be suitable for particular embodiments. In one embodiment, the first surface 280 of the biasing member 278 can be positioned a first distance from the surface 235 of the second portion 234 and the second surface 282 of the biasing member 278 can be positioned a second distance from the surface 235. In various embodiments, the second distance can be larger than the first distance. In one embodiment, the intermediate surface 284 can connect the first surface 280 and the second surface 282 and can slope downwardly from the second surface 282 toward the first surface 280, owing to the different heights of the first and second surfaces 280 and 282 with respect to the surface 235. In such an embodiment, the intermediate surface 284 can be used to apply a range of suitable forces to the biasing member 278 as the camming surface 224 moves over the intermediate surface 284.

The various surfaces can allow at least a portion of the biasing member 278 to be at least partially biased into the outer shell 214 when acted upon by the camming surface 224. As the portion of the biasing member 278, such as the projection portion 279, for example, is biased at least partially into the outer shell 214, it can apply a sufficient predetermined force against the membrane 50 to cause the membrane 50 to be pushed against a rupture element and/or a movable portion of the rupture element. As discussed above, the rupture element and/or the movable portion of the rupture element can comprise puncturing members. The puncturing members can be configured to pierce or puncture apertures in a rupturable seal attached to a volatile composition container or can pierce or puncture a wall of the volatile composition container to release the volatile composition onto the membrane 50 (or onto a wick and then onto the membrane 50) for evaporation.

In one non-limiting embodiment, as a user moves the mounting portion 222 from the first, non-actuated position (FIG. 16) to an intermediate, partially actuated position (FIG. 17) to the second, actuated position (FIG. 18), the camming surface 224 can engage the biasing surface of the biasing member 278. Optionally, the camming surface 224 can first contact the first surface 280 to slightly bias the biasing member 278 and/or the projection portion 279 a first distance inwards into the outer shell 214. In other embodiments, the camming surface 224 may not contact the first surface 280 and/or bias the biasing member 278 the first distance. Second, the camming surface 224 can then contact the sloped intermediate surface 284 to bias the biasing member 278 and/or the projection portion 279 a second distance inwards into the outer shell 214, which can cause the puncturing members to at least engage, and possibly puncture, the rupturable seal or the wall. Third, the camming surface 224 can then contact a first portion of the second surface 282 to bias the biasing member 278 and/or the projection portion 279 a third distance inwards into the outer shell 214, which can cause the puncturing members to puncture the rupturable seal or the wall. In other embodiments, when the camming surface 224 contacts the first portion of the second surface 282, the biasing member 278 and/or the projection portion 279 may not be biased any further inwards into the outer shell 214 than the second distance, for example. In any event, as the camming surface 224 moves along the second surface 282, it can become at least partially disengaged from contact with the second surface 282 and can at least partially enter the recess 228. Such movement can at least alleviate, and, in some embodiments eliminate, the predetermined force being applied by the camming surface 224 to the biasing member 278 and/or the projection portion 279, thereby alleviating or elimination the predetermined force being applied to the membrane, the rupture element, and/or the movable portion of the rupture element. As a result of the above, the puncturing members, owing to their attachment to the rupture element and/or the movable portion of the rupture element can be at least partially disengaged with the apertures in the rupturable seal or the wall and move towards the membrane 50 (or be biased toward the membrane) to allow the volatile composition to freely flow through the aperture and out of the volatile composition container. Stated another way, the puncturing members can be at least partially withdrawn from the rupturable seal or the wall to enlarge the area of the apertures available for flowing the volatile composition therethrough.

In essence, the biasing member 278 can allow the camming surface 224 to apply a sufficient predetermined force to the membrane 50, the rupture element, and/or the movable portion of the rupture element as the cam 220 is moved between the first, non-actuated position and the second, actuated position. In contrast to the various embodiments described above, however, the biasing element 278 can apply the sufficient predetermined force for a short period of time verses the entire time the cam 220/mounting portion 222 is in the second, actuated position. In such an embodiment, the force can be applied for a period of time of about 0.1 seconds to about 5 seconds, alternatively between about 0.5 seconds and about 2 seconds, and alternatively between about 1 second and about 2 seconds, for example. Those of skill in the art will recognize that the predetermined force can be applied for any suitable duration of time in which the rupturable seal or the wall can be sufficiently pierced or punctured to allow the release of the volatile composition from the volatile composition container.

In one non-limiting embodiment, a method of dispensing a volatile composition can comprise providing a volatile composition container comprising a volatile composition therein, and providing a rupture element positioned proximate to the volatile composition container. The method can also comprise actuating an actuator to move at least a portion of the rupture element and puncture the volatile composition container such that at least a portion of the volatile composition is released from the volatile composition container for evaporation. The method can also comprise providing a breathable membrane positioned proximate to the rupture element, and releasing the volatile composition onto the breathable membrane. In one embodiment, the method can comprise evaporating at least a portion of the volatile composition from the breathable membrane, and releasing the evaporated portion of the volatile composition to an atmosphere surrounding the volatile composition dispenser. The actuating described above can comprise moving the actuator between a first position, where the actuator does not apply a force to the rupture element, and a second position, wherein the actuator applies a force to the rupture element to move a portion of the rupture element toward the volatile composition container and puncture the volatile composition container or a rupturable seal. The method can also comprise biasing at least a portion of the rupture element away from the volatile composition container at least before the portion of the rupture element has punctured the volatile composition container or the rupturable seal. The method can further comprise providing a biasing member configured to apply a predetermined force to the rupture element, moving the actuator into a first, actuated position where the actuator engages the biasing member and applies a predetermined force to the portion of the rupture element, and moving the actuator into a second, actuated position where the actuator does not apply the predetermined force to the portion of the rupture element.

The volatile composition dispensers of the present disclosure can deliver the volatile composition 40 to the atmosphere surrounding the volatile composition dispensers in a continuous manner. The term "volatile composition" as used herein, can refer to a single or compound chemical or material that is vaporizable at or near room temperature and atmospheric pressure without the need for an external energy source. In one embodiment, the volatile composition 40 can be a material comprised entirely of a single volatile composition, for example. In another embodiment, the volatile composition can also comprise a composition that has one or more than one volatile components. As such, it is not necessary for all of the component materials of the composition to be volatile. Any suitable volatile composition in any amount or form, including a liquid and/or gel composition, can be used with the volatile composition dispensers of the present disclosure. Liquids and/or gels suitable for use herein can, thus, also have non-volatile components, such as carrier materials (e.g., water, solvents, etc.). It should also be understood that when the liquid is described herein as being "delivered", "emitted", "evaporated", or "released," this refers to the volatilization of the volatile component thereof, and does not require that the non-volatile components thereof be emitted.

In addition to the volatile composition 40, the volatile composition dispensers of the present disclosure can comprise any known malodor composition to neutralize odors, for example. Suitable malodor compositions can comprise cyclodextrin, reactive aldehydes and/or ionones, for example.

The volatile composition 40 can be in the form of perfume oil. Most conventional fragrance materials are volatile essential oils. The volatile composition 40 can be a volatile organic compound commonly available from perfumery suppliers. Furthermore, the volatile composition 40 can be comprised of synthetically or naturally formed materials. Examples can comprise, but are not limited to: oil of bergamot, bitter orange, lemon, mandarin, caraway, cedar leaf, clove leaf, cedar wood, geranium, lavender, orange, origanum, petitgrain, white cedar, patchouli, neroili, rose absolute, and any other suitable materials. In the case of air fresheners or fragrances, the different volatile compositions can be similar, related, complementary, or contrasting.

In one non-limiting embodiment, the volatile composition 40 can also originate in the form of a crystalline solid, which has the ability to sublime into the vapor phase at ambient temperatures or be used to fragrance a liquid. Any suitable crystalline solid in any suitable amount or form can be used with the volatile composition dispensers of the present disclosure. For example, suitable crystalline solids can comprise but are not limited to: vanillin, ethyl vanillin, coumarin, tonalid, calone, heliotropene, musk xylol, cedrol, musk ketone benzohenone, raspberry ketone, methyl naphthyl ketone beta, phenyl ethyl salicylate, veltol, maltol, maple lactone, proeugenol acetate, evemyl, and the like. It may not be desirable, however, for volatile compositions to be closely similar if different volatile compositions are being used in an attempt to avoid the problem of emission habituation. Otherwise, the people experiencing the emissions may not notice that a different material is being emitted. The different emissions can be provided using a plurality of delivery systems each providing a different volatile composition (such as, musk, floral, fruit emissions, etc). The different emissions can be related to each other by a common theme, or in some other manner. An example of emissions that are different, but complementary might be a cinnamon emission and an apple emission.

While not wishing to be bound by theory, the continuous delivery of the volatile compositions can be a function of various factors including membrane pore size, membrane surface area, the physical properties of the volatile composition such as molecular weight, for example, saturation vapor pressure ("VP"), and viscosity and/or surface tension of the volatile composition containing composition.

In one non-limiting embodiment, the composition can be engineered such that the composition comprises about 10% to about 100%, by total weight, of volatile compositions that individually comprise a VP at 25° C. of less than about 0.01 torr, alternatively about 40% to about 100% of volatile compositions that individually have a VP at 25° C. less than about 0.1 torr, alternatively about 50% to about 100% of volatile compositions that individually have a VP at 25° C. less than about 0.1 torr, and alternatively about 90% to about 100% of volatile compositions that individually have a VP at 25° C. of less than about 0.3 torr, for example. In one embodiment, the composition can comprise about 0% to about 15%, by total weight, of volatile compositions that individually have a VP at 25° C. of about 0.004 torr to about 0.035 torr; and about 0% to about 25%, by total weight, of volatile compositions that individually have a VP at 25° C. of about 0.1 torr to about 0.325 torr; and about 65% to about 100%, by total weight, of volatile compositions that individually have a VP at 25° C. of about 0.035 torr to about 0.1 torr, for example.

The VP of individual volatile compositions in two example compositions are set forth below in Tables 1 and 2. These compositions are shown by way of illustration and are not intended to be in any way limiting of the present disclosure.

TABLE 1

| Wt % | Low VP (torr) | High VP (torr) |
| --- | --- | --- |
| 27.71 | 0.175 | 0.325 |
| 20.78 | 0.0875 | 0.1125 |
| 13.86 | 0.0625 | 0.0875 |
| 8.66 | 0.0375 | 0.0625 |
| 8.66 | 0.0175 | 0.0325 |
| 6.93 | 0.00875 | 0.01125 |
| 6.93 | 0.00625 | 0.00875 |
| 3.18 | 0.00375 | 0.00625 |
| 1.27 | 0.00175 | 0.00325 |
| 0.95 | 0.000875 | 0.001125 |
| 0.64 | 0.000625 | 0.000875 |
| 0.32 | 0.000375 | 0.000625 |
| 0.09 | 0.000175 | 0.000325 |

TABLE 2

| Wt % | Low VP (torr) | High VP (torr) |
| --- | --- | --- |
| 33.38 | 0.175 | 0.325 |
| 25.75 | 0.0875 | 0.1126 |
| 19.07 | 0.0625 | 0.0875 |
| 13.86 | 0.0375 | 0.0625 |
| 4.00 | 0.0175 | 0.0325 |
| 1.50 | 0.00875 | 0.01125 |
| 0.50 | 0.00625 | 0.00875 |
| 0.72 | 0.00375 | 0.00625 |
| 0.55 | 0.00175 | 0.00325 |
| 0.27 | 0.000875 | 0.001125 |
| 0.20 | 0.000625 | 0.000875 |
| 0.13 | 0.000375 | 0.000625 |
| 0.07 | 0.000175 | 0.000325 |

The viscosity of the volatile composition 40 may control how and when it is delivered to the membrane 50. For example, less viscous volatile compositions may flow faster than the more viscous volatile compositions. Thus, the membrane 50 can be first wetted with the less viscous materials. The more viscous volatile composition, being slightly less or of similar density with the less viscous phase, may remain in a collection basin or the volatile composition container 38 via gravity. Thus, the less viscous volatile composition can be delivered to the membrane 50 and emitted to the atmosphere more quickly. To help prevent liquid from seeping through the membrane 50, volatile compositions may have viscosities less than about 23 CP and surface tension less than about 33 mN/m, for example. In one embodiment, the volatile composition 40 can have a viscosity of about 1.0 CP to less than about 25 CP, alternatively about 1.0 CP to less than about 23 CP, and alternatively about 1.0 CP to less than about 15 CP, for example. The composition can be designed such that the volatile composition 40 can comprise a surface tension of about 19 mN/m to less than about 33 mN/m, alternatively about 19 mN/m to less than about 30 mN/m, and alternatively about 19 mN/m to less than about 27 mN/m, for example.

Non-Limiting Example of a Suitable Microporous Membrane

As used in this example, the "volatile material contact surface" is that surface of the microporous membrane that faces and typically is in contact with volatile material, which is, for example, contained in a test reservoir, as described in further detail below.

As used in this example, the "vapor release surface" is that surface of the microporous membrane that does not face and/or contact directly the volatile material, and from which volatile material is released into an exterior atmosphere in a gaseous or vapor form.

As used in this example, the term "(meth)acrylate" and similar terms, such as "esters of (meth)acrylic acid" means acrylates and/or methacrylates.

As used in this example, the "volatile material transfer rate" of the microporous membrane, is determined in accordance with the following description. A test reservoir is fabricated from a clear thermoplastic polymer, having interior volume sufficient to contain 2 milliliters of volatile material such as benzyl acetate. The interior dimensions of the reservoir is defined by a circular diameter at the edge of the open face of approximately 4 centimeters and a depth of no greater than 1 centimeter. The open face is used to determine the volatile material transfer rate. With the test reservoir laying flat (with the open face facing upward), about 2 milliliters of benzyl acetate is introduced into the test reservoir. With benzyl acetate introduced into the test reservoir, a sheet of microporous membrane having a thickness of from 6 to 18 mils is placed over the open face/side of the test reservoir, such that 10 cm$^2$ of the volatile material contact surface of the microporous sheet is exposed to the interior of the reservoir. The test reservoir is weighed to obtain an initial weight of the entire charged assembly. The test reservoir, containing benzyl acetate and enclosed with the sheet of microporous membrane, is then placed, standing upright, in a laboratory chemical fume hood having approximate dimensions of 5 feet (height)×5 feet (width)×2 feet (depth). With the test reservoir standing upright, benzyl acetate is in direct contact with at least a portion of the volatile material contact surface of the microporous sheet. The glass doors of the fume hood are pulled down, and the air flow through the hood is adjusted so as to have eight (8) turns (or turnovers) of hood volume per hour. Unless otherwise indicated, the temperature in the hood is maintained at 25° C.±5° C. The humidity within in the fume hood is ambient. The test reservoirs are regularly weighed in the hood. The calculated weight loss of benzyl acetate, in combination with the elapsed time and surface area of the microporous sheet exposed to the interior of the test reservoir, are used to determine the volatile transfer rate of the microporous sheet, in units of mg/(hour, cm$^2$).

As used in this example, the percent increase in volatile material transfer rate of the microporous membrane of the present invention from 25° C. to 60° C. is determined for separate but substantially equivalent microporous membrane sheet samples at 25° C. and 60° C., in accordance with the method described above. Reservoirs are placed in a large glass bell jar and over a 50% aqueous solution of potassium chloride also contained in the bell jar. The entire bell jar with contents is placed in an oven heated to 60° C. The reservoirs are held under these conditions for a period of 7 to 10 hours. The reservoirs are then returned to the hood at ambient conditions overnight and the process is repeated over several days. Each of the reservoirs is weighed before being placed in the bell jar and after being removed from the bell jar. Upon removal from the bell jar, the weight of each reservoir is taken after the reservoir had returned to ambient temperature.

As used in this example, whether the vapor release surface of the microporous membrane is "substantially free of volatile material in liquid form" is determined in accordance with the following description. When the test reservoirs are weighed, as described above, the vapor release surface of the microporous sheet is examined visually by naked eye to determine if drops and/or a film of liquid were present thereon. If any evidence of drops (i.e., a single drop) and/or a film of liquid is visually observed on the vapor release surface, but does not run off the surface, the microporous sheet is considered to be acceptable. If the drops run off the surface, the microporous sheet is determined to have failed. If no evidence of drops (i.e., not one drop) and/or a film of liquid is visually observed on the vapor release surface, the microporous sheet is determined to be substantially free of volatile material in liquid form.

Unless otherwise indicated, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 6.1, 3.5 to 7.8, 5.5 to 10, etc.

Unless otherwise indicated, all numbers or expressions, such as those expressing structural dimensions, quantities of ingredients, etc., as used in the specification and claims are understood as modified in all instances by the term "about."

The term "volatile material" as in this example means a material that is capable of conversion to a gaseous or vapor form (i.e., capable of vaporizing) at ambient room temperature and pressure, in the absence of imparted additional or supplementary energy (e.g., in the form of heat and/or agitation). The volatile material can comprise an organic volatile material, which can include those volatile materials comprising a solvent-based material, or those which are dispersed in a solvent-based material. The volatile material may be in a liquid form and/or in a solid form, and may be naturally occurring or synthetically formed. When in a solid form, the volatile material typically sublimes from solid form to vapor form, in the absence of an intermediate liquid form. The volatile material may optionally be combined or formulated with nonvolatile materials, such as a carrier (e.g., water and/or nonvolatile organic solvents). In the case of a solid volatile material, the nonvolatile carrier may be in the form of a porous material (e.g., a porous inorganic material) in which the solid volatile material is held. Also, the solid volatile material may be in the form of a semi-solid gel.

The volatile material transfer rate of the microporous membrane can be less than or equal to 0.7 mg/(hour*cm$^2$), or less than or equal to 0.6 mg/(hour*cm$^2$), or less than or equal to 0.55 mg/(hour*cm$^2$), or less than or equal to 0.50 mg/(hour*cm$^2$). The volatile material transfer rate of the microporous membrane can be equal to or greater than 0.02 mg/(hour*cm$^2$), or equal to or greater than 0.04 mg/(hour*cm$^2$), or equal to or greater than 0.30 mg/(hour*cm$^2$), or equal to or greater than 0.35 mg/(hour*cm$^2$). The volatile material transfer rate of the microporous membrane may range between any combination of these upper and lower values. For example, the volatile material transfer rate of the microporous membrane can be from 0.04 to 0.6 mg/(hour*cm$^2$), or from 0.2 to 0.6 mg/(hour*cm$^2$), or from 0.30 to 0.55 mg/(hour*cm$^2$), or from 0.35 to 0.50 mg/(hour*cm$^2$), in each case inclusive of the recited values.

While not intending to be bound by any theory, when volatile material is transferred from the volatile material contact surface to the vapor release surface of the microporous membrane, it is believed that the volatile material is in a form selected from liquid, vapor, and a combination thereof. In addition, and without intending to be bound by any theory, it is believed that the volatile material, at least in part, moves through the network of interconnecting pores that communicate substantially throughout the microporous membrane.

The microporous membrane can have a density of at least 0.7 g/cm$^3$, such as at least 0.8 g/cm$^3$. The density of the microporous membrane may be determined by measuring the weight and volume of a sample of the microporous membrane. The upper limit of the density of the microporous membrane may range widely, provided it has a targeted volatile material transfer rate of, for example, from 0.04 to 0.6 mg/(hour*cm$^2$), and the vapor release surface is substantially free of volatile material in liquid form when volatile material is transferred from the volatile material contact surface to said vapor release surface. Typically, the density of the microporous membrane is less than or equal to 1.5 g/cm$^3$, or less than or equal to 1.2 g/cm$^3$, or less than or equal to 1.0 g/cm$^3$. The microporous membrane can have a density of from 0.7 g/cm$^3$ to 1.5 g/cm$^3$, for example, from 0.8 g/cm$^3$ to 1.2 g/cm$^3$, inclusive of the recited values.

When the microporous membrane has a density of at least 0.7 g/cm$^3$, such as at least 0.8 g/cm$^3$, the volatile material contact surface and the vapor release surface of the microporous membrane each may be free of a coating material thereon. When free of a coating material thereon, the volatile material contact surface and the vapor release surface each are defined by the microporous membrane.

When the microporous membrane has a density of at least 0.7 g/cm$^3$, such as at least 0.8 g/cm$^3$, at least a portion of the volatile material contact surface of the microporous membrane optionally may have a first coating thereon, and/or at least a portion of the vapor release surface of the microporous membrane optionally may have a second coating thereon. The first coating and the second coating may be the same or different. When at least a portion of the volatile material contact surface has a first coating thereon, the volatile material contact surface is defined at least in part by the first coating. When at least a portion of the vapor release surface has a second coating thereon, the vapor release surface is defined at least in part by the second coating.

The first coating and the second coating may each be selected from liquid coatings and solid particulate coatings (e.g., powder coatings). Typically, each of the first and second coatings independently is selected from liquid coatings which may optionally include a solvent selected from water, organic solvents and combinations thereof. The first and second coatings each independently may be selected from crosslinkable coatings (e.g., thermosetting coatings and photo-curable coatings), and non-crosslinkable coatings (e.g., air-dry coatings). The first and second coatings may be applied to the respective surfaces of the microporous membrane in accordance with art-recognized methods, such as spray application, curtain coating, dip coating, and/or drawn-down coating (e.g., by means of a doctor blade or draw-down bar) techniques.

The first and second coating compositions each independently can include art-recognized additives, such as antioxidants, ultraviolet light stabilizers, flow control agents, dispersion stabilizers (e.g., in the case of aqueous dispersions), and colorants (e.g., dyes and/or pigments). Typically, the first and second coating compositions are free of colorants, and are as such substantially clear or opaque. Optional additives may be present in the coating compositions in individual amounts of from, for example, 0.01 to 10 percent by weight, based on the total weight of the coating composition.

The first coating and said second coating each independently can be formed from an aqueous coating composition that includes dispersed organic polymeric material. The aqueous coating composition may have a particle size of from 200 to 400 nm. The solids of the aqueous coating composition may vary widely, for example from 0.1 to 30 percent by weight, or from 1 to 20 percent by weight, in each case based on total weight of the aqueous coating composition. The organic polymers of the aqueous coating compositions may have number average molecular weights (Mn) of, for example, from 1000 to 4,000,000, or from 10,000 to 2,000,000.

The aqueous coating composition can be selected from aqueous poly(meth)acrylate dispersions, aqueous polyurethane dispersions, aqueous silicone (or silicon) oil dispersions, and combinations thereof. The poly(meth)acrylate polymers of the aqueous poly(meth)acrylate dispersions may be prepared in accordance with art-recognized methods. For example, the poly(meth)acrylate polymers may include residues (or monomer units) of alkyl (meth)acrylates having from 1 to 20 carbon atoms in the alkyl group. Examples of alkyl (meth)acrylates having from 1 to 20 carbon atoms in the alkyl group include, but are not limited to, methyl (meth)acrylate, ethyl (meth)acrylate, 2-hydroxyethyl (meth)acrylate, propyl (meth)acrylate, 2-hydroxypropyl (meth)acrylate, isopropyl (meth)acrylate, butyl (meth)acrylate, isobutyl (meth)acrylate, tert-butyl (meth)acrylate, 2-ethylhexyl (meth)acrylate, lauryl (meth)acrylate, isobornyl (meth)acrylate, cyclohexyl (meth)acrylate, and 3,3,5-trimethylcyclohexyl (meth)acrylate. For purposes of non-limiting illustration, an example of an aqueous poly(meth)acrylate dispersion from which the first and second coating compositions may each be independently selected is HYCAR 26138, which is commercially available from Lubrizol Advanced Materials, Inc.

The polyurethane polymers of the aqueous polyurethane dispersions, from which the first and second coatings each independently may be selected, include any of those known to the skilled artisan. Typically the polyurethane polymers are prepared from isocyanate functional materials having two or more isocyanate groups, and active hydrogen functional materials having two or more active hydrogen groups. The active hydrogen groups may be selected from, for example, hydroxyl groups, thiol groups, primary amines, secondary amines, and combinations thereof. For purposes of non-limiting illustration, an example of an aqueous polyurethane dispersion from which the first and second coating compositions may each be independently selected is WIT-COBOND W-240, which is commercially available from Chemtura Corporation.

The silicon polymers of the aqueous silicone oil dispersions may be selected from known and art-recognized aqueous silicone oil dispersions. For purposes of non-limiting illustration, an example of an aqueous silicon dispersion from which the first and second coating compositions may each be independently selected is MOMENTIVE LE-410, which is commercially available from Momentive Performance Materials.

The first coating and the second coating each independently can be applied at any suitable thickness, provided the microporous membrane has a targeted volatile material transfer rate of, for example, from 0.04 to 0.6 mg/(hour*cm$^2$), and the vapor release surface is substantially free of volatile material in liquid form when volatile material is transferred from the volatile material contact surface to said vapor release surface. Also, the first coating and the second coating each independently can have a coating weight (i.e., the coating on the microporous membrane) of from 0.01 to 5.5 g/m$^2$, such as from 0.1 to 5.0 g/m$^2$, or from 0.5 to 3 g/m$^2$, or from 0.75 to 2.5 g/m$^2$, or from 1 to 2 g/m$^2$.

The microporous membrane can have a density of less than 0.8 g/cm$^3$, and at least a portion of the volatile material contact surface of the microporous membrane can have a first coating thereon, and/or at least a portion of the vapor release surface of the microporous membrane can have a second coating thereon. The first coating and the second coating may be the same or different, and each independently is as described previously herein with regard to the optional first and second coatings of the microporous membrane having a density of at least 0.7 g/cm$^3$.

When less than 0.7 g/cm$^3$, the density of the microporous membrane of the present invention may have any suitable lower limit, provided the microporous membrane has a targeted volatile material transfer rate of, for example, from 0.04 to 0.6 mg/(hour*cm$^2$), and the vapor release surface is substantially free of volatile material in liquid form when volatile material is transferred from the volatile material contact surface to said vapor release surface. With this particular embodiment of the present invention, the density of the microporous membrane may be from 0.6 to less than 0.8 g/cm$^3$, or from 0.6 to 0.75 g/cm$^3$ (e.g., from 0.60 to 0.75 g/cm$^3$) or from 0.6 to 0.7 g/cm$^3$ (e.g., from 0.60 to 0.70 g/cm$^3$), or from 0.65 to 0.70 g/cm$^3$.

Further, at least a portion of the volatile material contact surface of the microporous membrane can have a first coating thereon, and/or at least a portion of the vapor release surface of the microporous membrane can have a second coating thereon, in which each of the first and second coatings independently is selected from a coating composition comprising a poly(vinyl alcohol).

With the poly(vinyl alcohol) coated embodiment of the present invention, when the microporous membrane (i.e., the poly(vinyl alcohol) coated microporous membrane) is exposed to a temperature increase of from 25° C. to 60° C., the volatile material transfer rate thereof increases by less than or equal 150 percent. When the poly(vinyl alcohol) coated microporous membrane) is exposed to a temperature increase (e.g., from an ambient temperature of from 25° C. to 60° C.) the volatile material transfer rate typically increases, and typically does not decrease unless, for example, the microporous membrane has been damaged by exposure to the higher ambient temperature. As such, and as used herein and in the claims, the statement "the volatile material transfer rate thereof increases by less than or equal to [a stated] percent" (e.g., 150 percent), is inclusive of a lower limit of 0 percent, but is not inclusive of a lower limit that is less than 0 percent.

For purposes of illustration, when the poly(vinyl alcohol) coated microporous membrane has a volatile material transfer rate of 0.3 mg/(hour*cm$^2$) at 25° C., when the microporous membrane is exposed to a temperature of 60° C., the volatile material transfer rate increases to a value that is less than or equal to 0.75 mg/(hour*cm$^2$).

In an embodiment of the present invention, when the microporous membrane (i.e., the poly(vinyl alcohol) coated microporous membrane) is exposed to a temperature increase of from 25° C. to 60° C., the volatile material transfer rate thereof increases by less than or equal 125 percent. For example, when the poly(vinyl alcohol) coated microporous membrane has a volatile material transfer rate of 0.3 mg/(hour*cm$^2$) at 25° C., when the microporous membrane is exposed to a temperature of 60° C., the volatile material transfer rate increases to a value that is less than or equal to 0.68 mg/(hour*cm$^2$).

Further, when the microporous membrane (i.e., the poly(vinyl alcohol) coated microporous membrane) is exposed to a temperature increase of from 25° C. to 60° C., the volatile material transfer rate thereof increases by less than or equal 100 percent. For example, when the poly(vinyl alcohol) coated microporous membrane has a volatile material transfer rate of 0.3 mg/(hour*cm$^2$) at 25° C., when the microporous membrane is exposed to a temperature of 60° C., the volatile material transfer rate increases to a value that is less than or equal to 0.6 mg/(hour*cm$^2$).

The first and second poly(vinyl alcohol) coatings each independently may be present in any suitable coating weight, provided the microporous membrane has a targeted volatile material transfer rate of, for example, at least 0.04 mg/(hour*cm$^2$), and when the microporous membrane (i.e., the poly(vinyl alcohol) coated microporous membrane) is exposed to a temperature increase of from 25° C. to 60° C., the volatile material transfer rate thereof increases by less than or equal to 150 percent. Typically, the first poly(vinyl alcohol) coating and the second poly(vinyl alcohol) coating each independently have a coating weight of from 0.01 to 5.5 g/m$^2$, such as from 0.1 to 4.0 g/m$^2$, or from 0.5 to 3.0 g/m$^2$, or from 0.75 to 2.0 g/m$^2$.

The volatile material transfer rate of the poly(vinyl alcohol) coated microporous membrane can be at least 0.02 mg/(hour*cm$^2$). The volatile material transfer rate of the poly(vinyl alcohol) coated microporous membrane may be equal to or greater than 0.04 mg/(hour*cm$^2$), or equal to or greater than 0.1 mg/(hour*cm$^2$), or equal to or greater than 0.2 mg/(hour*cm$^2$), equal to or greater than 0.30 mg/(hour*cm$^2$), or equal to or greater than 0.35 mg/(hour*cm$^2$). The volatile material transfer rate of the poly(vinyl alcohol) coated microporous membrane may be less than or equal to 0.7 mg/(hour*cm$^2$), or less than or equal to 0.6 mg/(hour*cm$^2$), or less than or equal to 0.55 mg/(hour*cm$^2$), or less than or equal to 0.50 mg/(hour*cm$^2$). The volatile material transfer rate of the poly(vinyl alcohol) coated microporous membrane may range between any combination of these upper and lower values, inclusive of the recited values. For example, the volatile material transfer rate of the poly(vinyl alcohol) coated microporous membrane can be at least 0.02 mg/(hour*cm$^2$), such as from 0.04 to 0.70 mg/(hour*cm$^2$), or from 0.04 to 0.60 mg/(hour*cm$^2$), or from 0.20 to 0.60 mg/(hour*cm$^2$), or from 0.30 to 0.55 mg/(hour*cm$^2$), or from 0.35 to 0.50 mg/(hour*cm$^2$), in each case inclusive of the recited values.

The density of the microporous membrane of the poly(vinyl alcohol) coated microporous membrane of the present invention may vary widely, provided that the poly(vinyl alcohol) coated microporous membrane has a targeted volatile material transfer rate, for example, of at least 0.04 mg/(hour*cm$^2$), and when the microporous membrane (i.e., the poly(vinyl alcohol) coated microporous membrane) is exposed to a temperature increase of from 25° C. to 60° C., the volatile material transfer rate thereof increases by less than or equal to 150 percent.

Further, the density of the microporous membrane, of the poly(vinyl alcohol) coated microporous membrane, may be at least 0.7 g/cm$^3$, such as at least 0.8 g/cm$^3$ (e.g., from 0.8 to 1.2 g/cm$^3$) all inclusive of the recited values. In an embodiment of the present invention, the density of the poly(vinyl alcohol) coated microporous membrane (i.e., the density of the microporous membrane prior to application of the poly(vinyl alcohol) coating) is less than 0.8 g/cm$^3$. For example, the density of the microporous membrane, of the poly(vinyl alcohol) coated microporous membrane, may be from 0.6 to less than 0.8 g/cm$^3$, or from 0.6 to 0.75 g/cm$^3$ (e.g., from 0.60 to 0.75 g/cm$^3$) or from 0.6 to 0.7 g/cm$^3$ (e.g., from 0.60 to 0.70 g/cm$^3$), or from 0.65 to 0.70 g/cm$^3$, all inclusive of the recited values.

With the poly(vinyl alcohol) coated microporous membrane of the present invention, when volatile material is transferred from the volatile material contact surface to the vapor release surface, the vapor release surface is substantially free of volatile material in liquid form.

The poly(vinyl alcohol) coating may be selected from liquid coatings which may optionally include a solvent selected from water, organic solvents and combinations thereof. The poly(vinyl alcohol) coating may be selected from crosslinkable coatings (e.g., thermosetting coatings), and non-crosslinkable coatings (e.g., air-dry coatings). The poly(vinyl alcohol) coating may be applied to the respective surfaces of the microporous membrane in accordance with art-recognized methods, such as spray application, curtain coating, or drawn-down coating (e.g., by means of a doctor blade or draw-down bar).

In an embodiment of the present invention, the first and second poly(vinyl alcohol) coatings are each independently formed from aqueous poly(vinyl alcohol) coating compositions. The solids of the aqueous poly(vinyl alcohol) coating composition may vary widely, for example from 0.1 to 15 percent by weight, or from 0.5 to 9 percent by weight, in each case based on total weight of the aqueous coating composition. The poly(vinyl alcohol) polymer of the poly(vinyl alcohol) coating compositions may have number average molecular weights (Mn) of, for example, from 100 to 1,000,000, or from 1000 to 750,000.

The poly(vinyl alcohol) polymer of the poly(vinyl alcohol) coating composition may be a homopolymer or copolymer. Co-monomer from which the poly(vinyl alcohol) copolymer may be prepared include those which are copolymerizable (by means of radical polymerization) with vinyl acetate, and which are known to the skilled artisan. For purposes of illustration, comonomers from which the poly(vinyl alcohol) copolymer may be prepared include, but are not limited to: (meth)acrylic acid, maleic acid, fumaric acid, crotonic acid, metal salts thereof, alkyl esters thereof (e.g., $C_2$-$C_{10}$ alkyl esters thereof), polyethylene glycol esters thereof, and polypropylene glycol esters thereof; vinyl chloride; tetrafluoroethylene; 2-acrylamido-2-methyl-propane sulfonic acid and its salts; acrylamide; N-alkyl acrylamide; N,N-dialkyl substituted acrylamides; and N-vinyl formamide.

For purposes of non-limiting illustration, an example of poly(vinyl alcohol) coating composition that may be used to form the poly(vinyl alcohol) coated microporous membrane of the present invention, is CELVOL 325, which is commercially available from Sekisui Specialty Chemicals.

The first and second poly(vinyl alcohol) coating compositions each independently can include art-recognized additives, such as antioxidants, ultraviolet light stabilizers, flow control agents, dispersion stabilizers (e.g., in the case of aqueous dispersions), and colorants (e.g., dyes and/or pigments). Typically, the first and second poly(vinyl alcohol) coating compositions are free of colorants, and are as such substantially clear or opaque. Optional additives may be present in the poly(vinyl alcohol) coating compositions in individual amounts of from, for example, 0.01 to 10 percent by weight, based on the total weight of the coating composition.

The matrix of the microporous membrane is composed of substantially water-insoluble thermoplastic organic polymer. Such polymers suitable for use as the matrix can widely vary. In general, any substantially water-insoluble thermoplastic organic polymer which can be extruded, calendered, pressed, or rolled into film, sheet, strip, or web may be used. The polymer may be a single polymer or it may be a mixture of polymers. The polymers may be homopolymers, copolymers, random copolymers, block copolymers, graft copolymers, atactic polymers, isotactic polymers, syndiotactic polymers, linear polymers, or branched polymers. When mixtures of polymers are used, the mixture may be homogeneous or it may comprise two or more polymeric phases.

Examples of classes of suitable substantially water-insoluble thermoplastic organic polymers include thermoplastic polyolefins, poly(halo-substituted olefins), polyesters, polyamides, polyurethanes, polyureas, poly(vinyl halides), poly(vinylidene halides), polystyrenes, poly(vinyl esters), polycarbonates, polyethers, polysulfides, polyimides, polysilanes, polysiloxanes, polycaprolactones, polyacrylates, and polymethacrylates. Hybrid classes, from which the water-insoluble thermoplastic organic polymers may be selected include, for example, thermoplastic poly(urethane-ureas), poly(ester-amides), poly(silane-siloxanes), and poly(ether-esters) are within contemplation. Further examples of suitable substantially water-insoluble thermoplastic organic polymers include thermoplastic high density polyethylene, low density polyethylene, ultrahigh molecular weight polyethylene, polypropylene (atactic, isotactic, or syndiotactic), poly(vinyl chloride), polytetrafluoroethylene, copolymers of ethylene and acrylic acid, copolymers of ethylene and methacrylic acid, poly(vinylidene chloride), copolymers of vinylidene chloride and vinyl acetate, copolymers of vinylidene chloride and vinyl chloride, copolymers of ethylene and propylene, copolymers of ethylene and butene, poly(vinyl acetate), polystyrene, poly(omega-aminoundecanoic acid) poly(hexamethylene adipamide), poly(epsilon-caprolactam), and poly(methyl methacrylate). The recitation of these classes and example of substantially water-insoluble thermoplastic organic polymers is not exhaustive, and are provided for purposes of illustration.

Substantially water-insoluble thermoplastic organic polymers may in particular include, for example, poly(vinyl chloride), copolymers of vinyl chloride, or mixtures thereof. In an embodiment the water-insoluble thermoplastic organic polymer includes an ultrahigh molecular weight polyolefin selected from: ultrahigh molecular weight polyolefin (e.g., essentially linear ultrahigh molecular weight polyolefin) having an intrinsic viscosity of at least 10 deciliters/gram; or ultrahigh molecular weight polypropylene (e.g., essentially linear ultrahigh molecular weight polypropylene) having an intrinsic viscosity of at least 6 deciliters/gram; or a mixture thereof. In a particular embodiment, the water-insoluble thermoplastic organic polymer includes ultrahigh molecular weight polyethylene (e.g., linear ultrahigh molecular weight polyethylene) having an intrinsic viscosity of at least 18 deciliters/gram.

Ultrahigh molecular weight polyethylene (UHMWPE) is not a thermoset polymer having an infinite molecular weight, it is technically classified as a thermoplastic. However, because the molecules are substantially very long chains, UHMWPE softens when heated but does not flow as a molten liquid in a normal thermoplastic manner. The very long chains and the peculiar properties they provide to UHMWPE are believed to contribute in large measure to the desirable properties of microporous membranes made using this polymer.

As indicated previously, the intrinsic viscosity of the UHMWPE is at least about 10 deciliters/gram. Usually the intrinsic viscosity is at least about 14 deciliters/gram. Often the intrinsic viscosity is at least about 18 deciliters/gram. In many cases the intrinsic viscosity is at least about 19 deciliters/gram. Although there is no particular restriction on the upper limit of the intrinsic viscosity, the intrinsic viscosity is frequently in the range of from about 10 to about 39 deciliters/gram. The intrinsic viscosity is often in the range of from about 14 to about 39 deciliters/gram. In most cases the intrinsic viscosity is in the range of from about 18 to about 39 deciliters/gram. An intrinsic viscosity in the range of from about 18 to about 32 deciliters/gram is preferred.

The nominal molecular weight of UHMWPE is empirically related to the intrinsic viscosity of the polymer according to the equation:

$$M(UHMWPE)=5.3\times10^4[\eta]^{1.37}$$

where M(UHMWPE) is the nominal molecular weight and [η] is the intrinsic viscosity of the UHMW polyethylene expressed in deciliters/gram.

As used herein and in the claims, intrinsic viscosity is determined by extrapolating to zero concentration the reduced viscosities or the inherent viscosities of several dilute solutions of the UHMWPE where the solvent is freshly distilled decahydronaphthalene to which 0.2 percent by weight, 3,5-di-tert-butyl-4-hydroxyhydrocinnamic acid, neopentanetetrayl ester [CAS Registry No. 6683-19-8] has been added. The reduced viscosities or the inherent viscosities of the UHMWPE are ascertained from relative viscosities obtained at 135.degree. C. using an Ubbelohde No. 1 viscometer in accordance with the general procedures of ASTM D 4020-81, except that several dilute solutions of differing concentration are employed. ASTM D 4020-81 is, in its entirety, incorporated herein by reference.

The matrix can comprise a mixture of substantially linear ultrahigh molecular weight polyethylene (UHMWPE) having an intrinsic viscosity of at least 10 deciliters/gram, and lower molecular weight polyethylene having an ASTM D 1238-86 Condition E melt index of less than 50 grams/10 minutes and an ASTM D 1238-86 Condition F melt index of at least 0.1 gram/10 minutes. The nominal molecular weight of the lower molecular weight polyethylene (LMWPE) is lower than that of the UHMWPE. LMWPE is thermoplastic and many different types are known. One method of classification is by density, expressed in grams/cubic centimeter and rounded to the nearest thousandth, in accordance with ASTM D 1248-84 (re-approved 1989), as summarized in the following Table 1.

TABLE 1

| Type | Abbreviation | Density (g/cm³) |
| --- | --- | --- |
| Low Density Polyethylene | LDPE | 0.910-0.925 |
| Medium Density Polyethylene | MDPE | 0.926-0.940 |
| High Density Polyethylene | HDPE | 0.941-0.965 |

Any or all of these polyethylenes may be used as the LMWPE in the microporous membrane of the present invention. For some applications, HDPE may be used because it ordinarily tends to be more linear than MDPE or LDPE. ASTM D 1248-84 (Reapproved 1989) is, in its entirety, incorporated herein by reference.

Processes for making the various LMWPE's are well known and well documented. They include the high pressure process, the Phillips Petroleum Company process, the Standard Oil Company (Indiana) process, and the Ziegler process. The ASTM D 1238-86 Condition E (that is, 190.degree. C. and 2.16 kilogram load) melt index of the LMWPE is less than about 50 grams/10 minutes. Often the Condition E melt index is less than about 25 grams/10 minutes. Preferably the Condition E melt index is less than about 15 grams/10 minutes. The ASTM D 1238-86 Condition F (that is, 190.degree. C. and 21.6 kilogram load) melt index of the LMWPE is at least 0.1 gram/10 minutes. In many cases the Condition F melt index is at least about 0.5 gram/10 minutes. Preferably the Condition F melt index is at least about 1.0 gram/10 minutes. ASTM D 1238-86 is, in its entirety, incorporated herein by reference.

Sufficient UHMWPE and LMWPE should be present in the matrix to provide their properties to the microporous membrane. Other thermoplastic organic polymer may also be present in the matrix so long as its presence does not materially affect the properties of the microporous membrane in an adverse manner. The other thermoplastic polymer may be one other thermoplastic polymer or it may be more than one other thermoplastic polymer. The amount of the other thermoplastic polymer which may be present depends upon the nature of such polymer. Examples of thermoplastic organic polymers which may optionally be present include poly(tetrafluoroethylene), polypropylene, copolymers of ethylene and propylene, copolymers of ethylene and acrylic acid, and copolymers of ethylene and methacrylic acid. If desired, all or a portion of the carboxyl groups of carboxyl-containing copolymers may be neutralized with sodium, zinc, or the like.

The UHMWPE and the LMWPE together can constitute at least 65 percent by weight of the polymer of the matrix, such as at least 85 percent by weight of the polymer of the matrix, or the UHMWPE and the LMWPE together can constitute substantially 100 percent by weight of the polymer of the matrix. The UHMWPE can constitute at least one percent by weight of the polymer of the matrix, and the UHMWPE and the LMWPE together constitute substantially 100 percent by weight of the polymer of the matrix.

Where the UHMWPE and the LMWPE together constitute 100 percent by weight of the polymer of the matrix of the microporous membrane, the UHMWPE can constitute greater than or equal to 40 percent by weight of the polymer of the matrix, such as greater than or equal to 45 percent by weight, or greater than or equal to 48 percent by weight, or greater than or equal to 50 percent by weight, or greater than or equal to 55 percent by weight of the polymer of the matrix. Also, the UHMWPE can constitute less than or equal to 99 percent by weight of the polymer of the matrix, such as less than or equal to 80 percent by weight, or less than or equal to 70 percent by weight, or less than or equal to 65 percent by weight, or less than or equal to 60 percent by weight of the polymer of the matrix. The level of UHMWPE comprising the polymer of the matrix can range between any of these values inclusive of the recited values.

Likewise, where the UHMWPE and the LMWPE together constitute 100 percent by weight of the polymer of the matrix of the microporous membrane, the LMWPE can constitute greater than or equal to 1 percent by weight of the polymer of the matrix, such as greater than or equal to 5 percent by weight, or greater than or equal to 10 percent by weight, or greater than or equal to 15 percent by weight, or greater than or equal to 20 percent by weight, or greater than or equal to 25 percent by weight, or greater than or equal to 30 percent by weight, or greater than or equal to 35 percent by weight, or greater than or equal to 40 percent by weight, or greater than or equal to 45 percent by weight, or greater than or equal to 50 percent by weight, or greater than or equal to 55 percent by weight of the polymer of the matrix. Also, the LMWPE can constitute less than or equal to 70 percent by weight of the polymer of the matrix, such as less than or equal to 65 percent by weight, or less than or equal to 60 percent by weight, or less than or equal to 55 percent by weight, or less than or equal to 50 percent by weight, or less than or equal to 45 percent by weight of the polymer of the matrix. The level of the LMWPE can range between any of these values inclusive of the recited values.

It should be noted that for any of the previously described microporous membranes of the present invention, the LMWPE can comprise high density polyethylene.

The microporous membrane also comprises a finely-divided, substantially water-insoluble particulate filler material. The particulate filler material may include an organic particulate material and/or an inorganic particulate material. The particulate filler material typically is not colored, for example, the particulate filler material is a white or off-white particulate filler material, such as a siliceous or clay particulate material.

The finely divided substantially water-insoluble filler particles may constitute from 20 to 90 percent by weight of the microporous membrane. For example, such filler particles may constitute from 20 to 90 percent by weight of the microporous membrane, such as from 30 percent to 90 percent by weight of the microporous membrane, or from 40 to 90 percent by weight of the microporous membrane, or from 40 to 85 percent by weight of the microporous membrane, or from 50 to 90 percent by weight of the microporous membrane and even from 60 percent to 90 percent by weight of the microporous membrane.

The finely divided substantially water-insoluble particulate filler may be in the form of ultimate particles, aggregates of ultimate particles, or a combination of both. At least about 90 percent by weight of the filler used in preparing the microporous membrane has gross particle sizes in the range of from 0.5 to about 200 micrometers, such as from 1 to 100 micrometers, as determined by the use of a laser diffraction particle size instrument, LS230 from Beckman Coulton, capable of measuring particle diameters as small as 0.04 micron. Typically, at least 90 percent by weight of the particulate filler has gross particle sizes in the range of from 10 to 30 micrometers. The sizes of the filler agglomerates may be reduced during processing of the ingredients used to prepare the microporous membrane. Accordingly, the distribution of gross particle sizes in the microporous membrane may be smaller than in the raw filler itself.

Non-limiting examples of suitable organic and inorganic particulate materials, that may be used in the microporous membrane of the present invention, include those described in U.S. Pat. No. 6,387,519 B1 at column 9, line 4 to column 13, line 62, the cited portions of which are incorporated herein by reference.

In a particular embodiment of the present invention, the particulate filler material comprises siliceous materials. Non-limiting examples of siliceous fillers that may be used to prepare the microporous membrane include silica, mica, montmorillonite, kaolinite, nanoclays such as cloisite available from Southern Clay Products, talc, diatomaceous earth, vermiculite, natural and synthetic zeolites, calcium silicate, aluminum silicate, sodium aluminum silicate, aluminum polysilicate, alumina silica gels and glass particles. In addition to the siliceous fillers, other finely divided particulate substantially water-insoluble fillers optionally may also be employed. Non-limiting examples of such optional particulate fillers include carbon black, charcoal, graphite, titanium oxide, iron oxide, copper oxide, zinc oxide, antimony oxide, zirconia, magnesia, alumina, molybdenum disulfide, zinc sulfide, barium sulfate, strontium sulfate, calcium carbonate, and magnesium carbonate. In a non-limiting embodiment, the siliceous filler may include silica and any of the aforementioned clays. Non-limiting examples of silicas include precipitated silica, silica gel, fumed silica, and combinations thereof.

Silica gel is generally produced commercially by acidifying an aqueous solution of a soluble metal silicate, e.g., sodium silicate at low pH with acid. The acid employed is generally a strong mineral acid such as sulfuric acid or hydrochloric acid, although carbon dioxide can be used. Inasmuch as there is essentially no difference in density between the gel phase and the surrounding liquid phase while the viscosity is low, the gel phase does not settle out, that is to say, it does not precipitate. Consequently, silica gel may be described as a non-precipitated, coherent, rigid, three-dimensional network of contiguous particles of colloidal amorphous silica. The state of subdivision ranges from large, solid masses to submicroscopic particles, and the degree of hydration from almost anhydrous silica to soft gelatinous masses containing on the order of 100 parts of water per part of silica by weight.

Precipitated silica generally is produced commercially by combining an aqueous solution of a soluble metal silicate, ordinarily alkali metal silicate such as sodium silicate, and an acid so that colloidal particles of silica will grow in a weakly alkaline solution and be coagulated by the alkali metal ions of the resulting soluble alkali metal salt. Various acids may be used, including but not limited to mineral acids. Non-limiting examples of acids that may be used include hydrochloric acid and sulfuric acid, but carbon dioxide can also be used to produce precipitated silica. In the absence of a coagulant, silica is not precipitated from solution at any pH. In a non-limiting embodiment, the coagulant used to effect precipitation of silica may be the soluble alkali metal salt produced during formation of the colloidal silica particles, or it may be an added electrolyte, such as a soluble inorganic or organic salt, or it may be a combination of both.

Precipitated silicas are available in many grades and forms from PPG Industries, Inc. These silicas are sold under the Hi-Sil® tradename.

For purposes of the present invention, the finely divided particulate substantially water-insoluble siliceous filler can comprise at least 50 percent by weight (e.g., at least 65, at least 75 percent by weight), or at least 90 percent by weight of the substantially water-insoluble filler material. The siliceous filler may comprise from 50 to 90 percent by weight (e.g., from 60 to 80 percent by weight) of the particulate filler material, or the siliceous filler may comprise substantially all of the substantially water-insoluble particulate filler material.

The particulate filler (e.g., the siliceous filler) typically has a high surface area allowing the filler to carry much of the processing plasticizer composition used to produce the microporous membrane of the present invention. The filler particles are substantially water-insoluble and also can be substantially insoluble in any organic processing liquid used to prepare the microporous membrane. This can facilitate retention of the particulate filler within the microporous membrane.

The microporous membrane of the present may also include minor amounts (e.g., less than or equal to 5 percent by weight, based on total weight of the microporous membrane) of other materials used in processing, such as lubricant, processing plasticizer, organic extraction liquid, water, and the like. Further materials introduced for particular purposes, such as thermal, ultraviolet and dimensional stability, may optionally be present in the microporous membrane in small amounts (e.g., less than or equal to 15 percent by weight, based on total weight of the microporous membrane). Examples of such further materials include, but are not limited to, antioxidants, ultraviolet light absorbers, reinforcing fibers such as chopped glass fiber strand, and the like. The balance of the microporous membrane, exclusive of filler and any coating, printing ink, or impregnant applied for one or more special purposes is essentially the thermoplastic organic polymer.

The microporous membrane of the present invention, also includes a network of interconnecting pores, which communicate substantially throughout the microporous membrane. On a coating-free, printing ink free and impregnant-free basis, pores typically constitute from 35 to 95 percent by volume, based on the total volume of the microporous membrane, when made by the processes as further described herein. The pores may constitute from 60 to 75 percent by volume of the microporous membrane, based on the total volume of the microporous membrane. As used herein and in the claims, the porosity (also known as void volume) of the microporous membrane, expressed as percent by volume, is determined according to the following equation:

$$\text{Porosity}=100[1-d_1/d_2]$$

where, $d_1$ is the density of the sample, which is determined from the sample weight and the sample volume as ascertained from measurements of the sample dimensions; and $d_2$ is the density of the solid portion of the sample, which is determined from the sample weight and the volume of the solid portion of the sample. The volume of the solid portion of the microporous membrane is determined using a Quantachrome stereopycnometer (Quantachrome Corp.) in accordance with the operating manual accompanying the instrument.

The volume average diameter of the pores of the microporous membrane is determined by mercury porosimetry using an Autoscan mercury porosimeter (Quantachrome Corp.) in accordance with the operating manual accompanying the instrument. The volume average pore radius for a single scan is automatically determined by the porosimeter. In operating the porosimeter, a scan is made in the high pressure range (from 138 kilopascals absolute to 227 megapascals absolute). If 2 percent or less of the total intruded volume occurs at the low end (from 138 to 250 kilopascals absolute) of the high pressure range, the volume average pore diameter is taken as twice the volume average pore radius determined by the porosimeter. Otherwise, an additional scan is made in the low pressure range (from 7 to 165 kilopascals absolute) and the volume average pore diameter is calculated according to the equation:

$$d=2[v_1 r_1/w_1+v_2 r_2/w_2]/[v_1/w_1+v_2/w_2]$$

where, d is the volume average pore diameter; $v_1$ is the total volume of mercury intruded in the high pressure range; $v_2$ is the total volume of mercury intruded in the low pressure range; $r_1$ is the volume average pore radius determined from the high pressure scan; $r_2$ is the volume average pore radius determined from the low pressure scan; $w_1$ is the weight of the sample subjected to the high pressure scan; and $w_2$ is the weight of the sample subjected to the low pressure scan.

Generally on a coating-free, printing ink-free and impregnant-free basis, the volume average diameter of the pores of the microporous membrane is at least 0.02 micrometers, typically at least 0.04 micrometers, and more typically at least 0.05 micrometers. On the same basis, the volume average diameter of the pores of the microporous membrane is also typically less than or equal to 0.5 micrometers, more typically less than or equal to 0.3 micrometers, and further typically less than or equal to 0.25 micrometers. The volume average diameter of the pores, on this basis, may range between any of these values, inclusive of the recited values. For example, the volume average diameter of the pores of the microporous membrane may range from 0.02 to 0.5 micrometers, or from 0.04 to 0.3 micrometers, or from 0.05 to 0.25 micrometers, in each case inclusive of the recited values.

In the course of determining the volume average pore diameter by means of the above described procedure, the maximum pore radius detected may also be determined. This is taken from the low pressure range scan, if run; otherwise it is taken from the high pressure range scan. The maximum pore diameter of the microporous membrane is typically twice the maximum pore radius.

Coating, printing and impregnation processes can result in filling at least some of the pores of the microporous membrane. In addition, such processes may also irreversibly compress the microporous membrane. Accordingly, the parameters with respect to porosity, volume average diameter of the pores, and maximum pore diameter are determined for the microporous membrane prior to application of one or more of these processes.

Although the various volatile composition dispensers disclosed herein have been discussed for use in a vehicle, those of ordinary skill in the art will recognize other uses for the dispensers in other suitable environments. In one embodiment, the volatile composition dispensers can be used to dispense insecticide at a camp site and/or within a tent or cabin, for example. In other various embodiments, the volatile composition dispensers can be used in a home, a workplace, a locker, a storage space, and/or any other suitable place or environment where the volatile composition dispensers would have utility to a user.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description are, in relevant part, incorporated herein by reference; the citation of any document is not to be construed as an admission that it is prior art with respect to the present disclosure. To the extent that any meaning or definition of a term in this written document conflicts with any meaning or definition of the term in a document incorporated by reference, the meaning or definition assigned to the term in this written document shall govern.

While particular embodiments of the present disclosure have been illustrated and described, those of skill in the art will recognize that various other changes and modifications can be made without departing from the spirit and scope of the disclosure. It is therefore intended to cover in the appended claims all such changes and modifications that are within the scope of this disclosure.

What is claimed is:

1. A volatile composition dispenser comprising:
   a volatile composition container comprising at least one liquid volatile composition therein;
   a rupture element comprising an outer housing and a movable portion attached to the outer housing;
   a cam comprising a camming surface on one end and a mounting portion attached to or formed with the cam on the other end, wherein the mounting portion comprises a plurality of detents for mounting the dispenser to an air vent; and
   a breathable membrane having an outer surface and an inner surface, the outer surface is proximal to the camming surface and the inner surface is distal to the camming surface, wherein the rupture element, when in a non-actuated position, is disposed between the inner surface of the breathable membrane and the volatile composition container, and wherein the camming surface, when actuated, applies a force to the movable portion of the rupture element and displaces the movable portion of the rupture element towards the volatile composition container in a first direction; relative to the outer housing, to puncture the volatile composition container in the first direction and release the at least one liquid volatile composition from the volatile composition container such that the at least one liquid volatile composition evaporates and exits the volatile composition dispenser.

2. The dispenser of claim 1, wherein the inner surface of the breathable membrane receives the at least one liquid volatile composition after the movable portion of the rupture element punctures the volatile composition container.

3. The dispenser of claim 1, wherein the breathable membrane comprises a microporous membrane configured to receive the at least one liquid volatile composition for evaporation.

4. The dispenser of claim 1, comprising an outer shell, wherein the volatile composition container and the rupture element are positioned at least partially within the outer shell, wherein the cam is positioned outside of the outer shell when the camming surface does not apply a force to at least the portion of the rupture element, and wherein the camming surface is at least partially positioned within the outer shell when the camming surface applies a force to at least the portion of the rupture element.

5. The dispenser of claim 1, comprising a rupturable seal in sealed communication with a portion of the volatile composition container, wherein the rupture element is positioned proximate to the rupturable seal such that when the camming surface moves the movable portion of the rupture element toward the rupturable seal, the movable portion of the rupture element punctures the rupturable seal to allow the at least one liquid volatile composition to be released from the volatile composition container onto the breathable membrane.

6. The dispenser of claim 1, wherein the cam is pivotable between a first position, where the camming surface is free from applying a force to the rupture element, and a second position, where the camming surface contacts said breathable membrane.

7. The dispenser of claim 1, comprising an uppermost portion and a lowermost portion, wherein the rupture element comprises at least one puncturing tip configured to puncture the volatile composition container at least at a location proximate to the lowermost portion of the volatile composition container when the camming surface moves the movable portion of the rupture element toward the volatile composition container.

8. The dispenser of claim 1, comprising an outer shell, wherein the outer shell comprises at least one vent configured to be placed in fluid communication with the at least one liquid volatile composition.

* * * * *